US012423622B2

(12) United States Patent
Oono et al.

(10) Patent No.: US 12,423,622 B2
(45) Date of Patent: *Sep. 23, 2025

(54) GENERATIVE MACHINE LEARNING SYSTEMS FOR GENERATING STRUCTURAL INFORMATION REGARDING CHEMICAL COMPOUND

(71) Applicant: Preferred Networks, Inc., Tokyo (JP)

(72) Inventors: Kenta Oono, Tokyo (JP); Justin Clayton, Tokyo (JP); Nobuyuki Ota, Tokyo (JP)

(73) Assignee: Preferred Networks, Inc., Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/394,019

(22) Filed: Dec. 22, 2023

(65) Prior Publication Data
US 2024/0144092 A1    May 2, 2024

Related U.S. Application Data

(63) Continuation of application No. 17/000,746, filed on Aug. 24, 2020, now Pat. No. 11,900,225, which is a
(Continued)

(51) Int. Cl.
*G06N 20/00* (2019.01)
*G06N 3/047* (2023.01)
(Continued)

(52) U.S. Cl.
CPC .............. *G06N 20/00* (2019.01); *G06N 3/047* (2023.01); *G06N 7/01* (2023.01); *G16C 20/50* (2019.02); *G16C 20/70* (2019.02)

(58) Field of Classification Search
CPC .......... G06N 20/00; G06N 7/01; G16C 20/50; G16C 20/70
See application file for complete search history.

(56) References Cited

U.S. PATENT DOCUMENTS

| 5,425,128 A | 6/1995 | Morrison |
| 6,434,490 B1 | 8/2002 | Agrafiotis et al. |

(Continued)

FOREIGN PATENT DOCUMENTS

| EP | 2889791 | 7/2015 |
| WO | 2014/034577 | 3/2014 |

OTHER PUBLICATIONS

Chicco et al. "Deep Autoencoder Neural Networks for Gene Ontology Annotation Predictions", ACM-BCB 2014, pp. 533-540.*
(Continued)

*Primary Examiner* — Li Wu Chang
(74) *Attorney, Agent, or Firm* — IPUSA, PLLC

(57) ABSTRACT

A computer system includes one or more memories and one or more processors configured to cause a generative model to generate structural information regarding a chemical compound by inputting a latent representation into the generative model, wherein the generative model has been trained such that differences between structural information regarding other chemical compounds and reconstructions of the structural information regarding the other chemical compounds generated by the generative model are reduced, the reconstructions being generated by inputting latent representations into the generative model, the latent representations being generated based on the structural information regarding the other chemical compounds.

29 Claims, 20 Drawing Sheets

Related U.S. Application Data continuation of application No. 15/015,044, filed on Feb. 3, 2016, now Pat. No. 10,776,712.

(60) Provisional application No. 62/262,337, filed on Dec. 2, 2015.

(51) Int. Cl.
  *G06N 7/01* (2023.01)
  *G16C 20/50* (2019.01)
  *G16C 20/70* (2019.01)

(56) References Cited

U.S. PATENT DOCUMENTS

| | | | |
|---|---|---|---|
| 8,484,022 | B1 | 7/2013 | Vanhoucke |
| 8,704,832 | B2 | 4/2014 | Taylor et al. |
| 8,751,421 | B2 | 6/2014 | Anderson et al. |
| 8,875,286 | B2 | 10/2014 | Friedrichs et al. |
| 8,924,314 | B2 | 12/2014 | Kulkarni et al. |
| 8,949,170 | B2 | 2/2015 | Zadeh |
| 2014/0046879 | A1 | 2/2014 | MacLennan et al. |
| 2014/0201126 | A1 | 7/2014 | Zadeh et al. |
| 2014/0278130 | A1 | 9/2014 | Bowles et al. |
| 2014/0310218 | A1 | 10/2014 | Min et al. |
| 2015/0036889 | A1 | 2/2015 | Ananda Yogendran |
| 2016/0321559 | A1 | 11/2016 | Rose et al. |
| 2017/0161635 | A1 | 6/2017 | Oono et al. |
| 2018/0276348 | A1 | 9/2018 | Jamison et al. |
| 2021/0241176 | A1 | 8/2021 | Yoo et al. |

OTHER PUBLICATIONS

Petsalaki et al. "Accurate Prediction of Peptide Binding Sites on Protein Surfaces", PLoS computational Biology, 2009, pp. 1-10.*

Brubaker et al. "Building Proteins in a Day: Efficient 3D Molecular Reconstruction", arXiv:1504.03573v1 [cs.CV] Apr. 14, 2015, pp. 10.*

Abstract of Butera, J., et al., "Computer-Assisted Design and Synthesis of Novel Aldose Reductase Inhibitors," J. Med. Chem., Apr. 1989, pp. 757-765, vol. 32, No. 4, NCBI, 2 pages, [Online] [Retrieved in May 31, 2016] Retrieved from the Internet<URL:http://www.ncbi.nlm.nih.gov/pubmed/2539477>.

Kingma, Diederik P. et al., Semi-supervised Learning with Deep Generative Models, NIPS2014 [online], Dec. 13, 2014, pp. 1-9, [retrieved on Jan. 13, 2017], Retrieved from the Internet: <URL: http://papers.nips.cc/paper/5352-semi-supervised-learning-with-deep-generative-models>.

"Identifying an Unknown Compound by Solubility, Functional Group Tests and Spectral Analysis", The handout to Signature Lab Series ANAL 0727, Apr. 2015, pp. 15, <URL: https://www1.udel.edu/chem/CHEM322/Handouts/unknowns_lab_handout.pdf>.

Bengio, Y. et al., "Deep Generative Stochastic Networks Trainable by Backprop," 31st International Conference on Machine Learning (ICML 2014), Journal of Machine Learning Research, vol. 32, Jun. 21-26, 2014, Submitted Online Jun. 5, 2013, Latest Online Version May 24, 2014, 16 pages, Available at<URL:https://arxiv.org/abs/1306.1091v1>.

Dahl, G.E. et al., "Multi-Task Neural Networks for QSAR Predictions," Submitted Jun. 4, 2014, pp. 1-21, Available at<URL: http://arxiv.org/abs/1406.1231>.

Eslami, S.M.A. et al., "The Shape Boltzmann Machine: A Strong Model of Object Shape," International Journal of Computer Vision, 2012 IEEE Conference on Computer Vision and Pattern Recognition (CVPR), Jun. 16-21, 2012, pp. 406-413.

Hinton, G.E. et al., "A Fast Learning Algorithm for Deep Belief Nets," Neural Computation, Jul. 2006, Posted Online May 17, 2006, pp. 1527-1554, vol. 18, No. 7.

Hinton, G.E. et al., "Optimal Perceptual Inference," Proceedings of the IEEE Conference on Computer Vision and Pattern Recognition, Jun. 1983, pp. 448-453.

Hinton, G.E., "Training Products of Experts by Minimizing Contrastive Divergence," Neural Computation, Aug. 2002, pp. 1771-1800, vol. 14, No. 8.

Kingma, D.P. et al., "Auto-Encoding Variational Bayes," May 1, 2014, Submitted on Dec. 20, 2013, pp. 1-14, Available at<URL:https://arxiv.org/abs/1312.6114>.

Kingma, D.P. et al., "Semi-Supervised Learning with Deep Generative Models," Oct. 31, 2014, Submitted on Jun. 20, 2014, pp. 1-9, Available at<URL: http://arxiv.org/abs/1406.5298>.

Knight, W., "Deep Learning Catches On in New Industries, from Fashion to Finance," May 31, 2015, MIT Technology Review, 3 pages, [Online] [Retrieved on May 31, 2016], Retrieved from the Internet<URL:http://www.technologyreview.com/news/537806/deep-learningdeep-learning-catches-on-in-new-industries-from-fashion-to-finance/?utm_campaign=socialsync&utm_medium=social-post&utm_source=facebook.

Lee, S-I., "Learning Undirected Models," Lecture 18, Jun. 1, 2011, University of Washington, 18 pages, [Online] [Retrieved on May 31, 2016, Retrieved from the Internet<URL: https://courses.cs.washington.edu/courses/cse515/11sp/class18-learnmnet.pdf>.

Salakhutdinov, R. et al., "Deep Boltzmann Machines," Proceedings of the 12th International Conference on Artificial Intelligence and Statistics (AISTATS), 2009, 8 pages, Available at <URL:http://jmlr.org/proceedings/papers/v5/salakhutdinov09a.html>.

Lecture: Gregor, K. et al., "Variational Autoencoders and Deep Recurrent Attentive Writers," Mar. 5, 2015, [Not Enclosed], May be viewed at<URL:https://www.youtube.com/watch?v=P78QYjWh5sM>.

Lecture: Hinton, G., "Recent Developments in Deep Learning," Mar. 19, 2010, [Not Enclosed], May be viewed at<URL:https://www.youtube.com/watch?v=VdIURAu1-aU>.

"What is the difference between Deep Boltzmann Machine, Deep Belief Networks and Deep Auto-Encoders? Is there is tutorial which explains the difference between procedures for pre-training and fine-tuning the above networks? (pseudo code would be of additional help)," Quora, Comments Written Aug. 26, 2014, 4 pages, [Online] [Retrieved in May 31, 2016] Retrieved from the Internet<URL:http://www.quora.com/What-is-the-difference-between-Deep-Boltzmann-Machine-Deep-Belief-Networks-and-Deep-Auto-Encoders-Is-there-is-tutorial-which-explains-the-difference-between-procedures-for-pre-training-and-fine-tuning-the-above-networks-pseudo-code-would-be-of-additional-help>.

Abstract of Butera, J., et al., "Computer-Assisted Design and Synthesis of Novel Aldose Reductase Inhibitors," J. Med. Chem., Apr. 1989, pp. 757-765, vol. 32, No. 4, NCBI, 2 p. [Online] [Retrieved in May 31, 2016] Retrieved from the Internet<URL:http://www.ncbi.nlm.nih.gov/pubmed/2539477>.

"Dragon 7 Available Now," Home Page, Talete SRL, 2013, 1 page, [Online] [Retrieved in May 31, 2016] Retrieved from the Internet<URL:http://www.talete.mi.it/>.

"Cross Validated," Stack Exchange Inc., 2013, 7 pages, [Online] [Retrieved in May 31, 2016] Retrieved from the Internet<URL:http://stats.stackexchange.com/questions/114385/what-is-the-difference-between-convolutional-neural-networks-restricted-boltzma>.

Cheung et al., Discovering Hidden Factors of Variation in Deep Networks, retreived from Internet <https://arxiv.org/pdf/1412.6583.pdf> (Jun. 2015) at pp. 1-10 (Year: 2015).

Ramsundar, et al., Massively Multitask Networks for Drug Discovery, retrieved from Internet <https://arxiv.org/abs/1502.02072> at pp. 1-27 (Feb. 2015) (Year: 2015).

Lusci et al., Deep Architectures and Deep Learning in Chemoinformatics: The Prediction of Aqueous Solubility for Drug-like Molecules, J. Chem. Inf. Model vol. 53 at pp. 1563-1575 (2013) (Year: 2013).

PCT International Search Report and Written Opinion, PCT Application No. PCT/JP2016/085955, Jan. 24, 2017, six pages.

Kode Chemoinformatics, "Dragon 7.0 Tutorial," Date Unknown, 10 pages. [Online] [Retrieved on Mar. 13, 2019] Retrieved from the Internet <URL: https://chm.kode-solutions.net/products_dragon_tutorial.php#01>.

Kode Chemoinformatics, "Homepage," Date Unknown, three pages. [Online] [Retrieved on Mar. 13, 2019] Retrieved from the Internet <URL: https://chm.kode-solutions.net/index.php>.

(56) References Cited

OTHER PUBLICATIONS

Talete Srl, "Dragon 6 User's Manual," 2010, 107 pages. [Online] [Retrieved on Mar. 13, 2019] Retrieved from the internet <URL: http://www.talete.mi.it/help/dragon_help/>.

Makhzani et al., Adversarial Autoencoders, Nov. 2015, available from Internet < https://arxiv.org/abs/1511.05644> (Year: 2015).

"Explore Chemistry" Quickly find chemical information from authoritative sources [online], Retrieved from the Internet: <URL: https://pubchem.ncbi.nlm.nih.gov/>.

"List of molecular descriptors calculated by Dragon" [online], Retrieved from the Internet: < URL: http://www.talete.mi.it/products/dragon_molecular_descriptor_list.pdf> .

"Molecular properties calculated by dProperties" [online], Retrieved from the Internet: < URL: www.talete.mi.it/products/dproperties_molecular_descriptors.htm>.

"Molecular Descriptors" the free online resource [online], Retrieved from the Internet: < URL: www.moleculardescriptors.eu/softwares/softwares.htm>.

"Molecular fingerprints, background" [online], Retrieved from the Internet: < URL: www.dalkescientific.com/writings/diary/archive/2008/06/26/fingerprint_background.html>.

"Chemical Descriptors" [online], Retrieved from the Internet: <URL: http://vega.marionegri.it/wordpress/resources/chemical-descriptors>.

Kingma, Diederik P. et al., Semi-supervised Learning with Deep Generative Models, NIPS2014 [online], 2014.12.13, pp. 1-9, [retrieved on 2017.01.13], Retrieved from the Internet: < URL: http://papers.nips.cc/paper/5352-semi-supervised-learning-with-deep-generative-models>.

Tissera et al. "Deep extreme learning machines: supervised autoencoding architecture for classification", Neurocompting, 2016, pp. 42-49.

Kyaw-Zeyar Myint et al., "Molecular Fingerprint-Based Artificial Neural Networks QSAR for Ligand Biological Activity Predictions", Molecular Pharmaceutics, American Chemical Society, Oct. 2012, vol. 9, No. 10, pp. 2912-2923.

"Identifying an Unknown Compound by Solubility, Functional Group Tests and Spectral Analysis", The handout to Signature Lab Series ANAL 0727, Apr. 2015, p. 15, <URL: https://www1.udel.edu/chem/CHEM322/Handouts/unknowns_lab_handout.pdf>.

Davide Chicco et al., "Deep Autoencoder Neural Netwoks for Gene Ontology Annotation Predictions", ACM-BCB, 2014, pp. 533-540.

Liu Jian-wei et al., "Predicting Protein Structural Classes with Autoencoder Neural Networks", CCDC, 2013, pp. 1894-1899.

* cited by examiner

Generation: $p_\theta(x|Z)$

Inference: $q_\phi(Z|x)$

GENERATIVE MACHINE LEARNING SYSTEMS FOR GENERATING STRUCTURAL INFORMATION REGARDING CHEMICAL COMPOUND

CROSS-REFERENCE TO RELATED APPLICATIONS

This application is a continuation of U.S. patent application Ser. No. 17/000,746 filed on Aug. 24, 2020, which is in turn a continuation of U.S. patent application Ser. No. 15/015,044 filed on Feb. 3, 2016, which claims the benefit under 35 USC 119(e) of prior U.S. Provisional Patent Application No. 62/262,337, filed on Dec. 2, 2015. The entire contents of U.S. patent application Ser. No. 17/000, 746, U.S. patent application Ser. No. 15/015,044, and U.S. Provisional Patent Application No. 62/262,337 are hereby incorporated by reference.

BACKGROUND OF THE INVENTION

Exploration of lead compounds with desired properties typically comprises high throughput or virtual screening. These methods are slow, costly, and ineffective.

In high throughput screening, chemical compounds from a compound library are tested. However, compound libraries are huge and most of the candidates are not eligible to be selected as a hit compound. To minimize costs associated with this complicated approach, some screening methods utilize in silico methods, known as virtual screening. However, available virtual screening methods require tremendous computational power and they can be algorithmically poor and time consuming.

Further, current hit-to-lead exploration primarily comprises exhaustive screening from vast lists of chemical compound candidates. This approach relies on the expectation and hope that a compound with a set of desired properties will be found within existing lists of chemical compounds. Further, even when current screening methods successfully find lead compounds, it does not mean that these lead compounds can be used as drugs. It is not rare for candidate compounds to fail at later stage of clinical trial. One of the major reasons of failure is toxicity or side effects that are not revealed until experiments with animals or humans. Finally, these exploration models are slow and costly.

Because of the inefficiencies and limitations of existing methods, there is a need for drug design methods that directly generate candidate chemical compounds having the desired set of properties, such as binding to a target protein. There is yet another need for generating candidate chemical compounds lacking toxicity or side effects. There is a final need for predicting how candidate chemical compounds would interact off-target and/or with other targets.

SUMMARY OF THE INVENTION

In a first aspect, the methods and systems described herein relate to a computer system for generation of chemical compound representations. The system may comprise a probabilistic autoencoder. The probabilistic autoencoder may comprise a probabilistic encoder configured to encode chemical compound fingerprints as latent variables; a probabilistic decoder configured to decode latent representations and generate random variables over values of fingerprint elements; and/or one or more sampling modules configured to sample from a latent variable or a random variable. The system may be trained by feeding it chemical compound fingerprints and training labels associated with the chemical compound fingerprints and generating reconstructions of chemical compound fingerprints, wherein the system's training is constrained by the reconstruction error. The reconstruction error may comprise the negative likelihood that an encoded chemical compound representation is drawn from the random variable generated by the probabilistic decoder. The system may be trained to optimize, for example to minimize, the reconstruction error. In some embodiments, the training is constrained by a loss function comprising the reconstruction error and a regularization error. The probabilistic autoencoder may be trained to learn to approximate an encoding distribution. The regularization error may comprise a penalty associated with the complexity of the encoding distribution. The training may comprise minimizing the loss function. In some embodiments, the training labels comprise one or more label elements having predetermined values. In some embodiments, the system is configured to receive a target label comprising one or more label elements and generate chemical compound fingerprints that satisfy a specified value for each of the one or more label elements. In some embodiments, the training labels do not comprise the target label. In some embodiments, each chemical compound fingerprint uniquely identifies a chemical compound. In some embodiments, the training further constrains the total information flow between the probabilistic encoder and the probabilistic decoder. In some embodiments, the probabilistic encoder is configured to provide an output comprising a pair of a vector of means and a vector of standard deviations. In some embodiments, the sampling module is configured to receive the output of the encoder, define the latent variable based on the output of the encoder, and generate one or more latent representations, wherein the latent variable is modeled by a probability distribution. In some embodiments, the probability distribution is selected from the group consisting of Normal distribution, Laplace distribution, Elliptical distribution, Student's t distribution, Logistic distribution, Uniform distribution, Triangular distribution, Exponential distribution, Invertible cumulative distribution, Cauchy distribution, Rayleigh distribution, Pareto distribution, Weibull distribution, Reciprocal distribution, Gompertz distribution, Gumbel distribution, Erlang distribution, Logarithmic Normal distribution, Gamma distribution, Dirichlet distribution, Beta distribution, Chi-Squared distribution, F distribution, and variations thereof. In some embodiments, the probabilistic encoder comprises an inference model. In some embodiments, the inference model comprises a multi-layer perceptron. In some embodiments, the probabilistic autoencoder comprises a generative model. In some embodiments, the generative model comprises a multi-layer perceptron. In some embodiments, the system further comprises a predictor that is configured to predict values of selected label elements for chemical compound fingerprints. In some embodiments, the label comprise one or more label elements selected from the group consisting of bioassay results, toxicity, cross-reactivity, pharmacokinetics, pharmacodynamics, bioavailability, and solubility.

In another aspect, the systems and methods described herein relate to a training method for generation of chemical compound representations. The training method may comprise training a generative model. The training of the training model may comprise inputting to the generative model chemical compound fingerprints and associated training labels, and generating reconstructions of chemical compound fingerprints. The generative model may comprise a probabilistic autoencoder comprising a probabilistic encoder configured to encode chemical compound fingerprints as latent variables; a probabilistic decoder configured to decode latent representations as random variables over values of fingerprint elements; and/or a sampling module configured to sample from the latent variables to generate latent representations or from a random variable to generate a reconstruction of a fingerprint. The training labels may comprise one or more label elements having empirical or predicted values. The system's training may be constrained by a reconstruction error. The reconstruction error may comprise the negative likelihood that an encoded chemical compound representation is drawn from the random variable output by the probabilistic decoder. The training may comprise minimizing the reconstruction error. In some embodiments, the training is constrained by a loss function comprising the reconstruction error and a regularization error. The training may comprise minimizing the loss function.

In yet another aspect, the methods and systems described herein relate to a computer system for drug prediction. The system may comprise a machine learning model comprising a generative model. The generative model may be trained with a training data set comprising chemical compound fingerprint data and associated training labels comprising one or more label elements. In some embodiments, the generative model comprises a neural network having at least 2, 3, 4, 5, 6, 7, 8, 9, 10, 11, 12, 13, 14, 15, 16, 17, 18, 19, 20, or more layers of units. In some embodiments, the label elements comprise one or more elements selected from the group consisting of bioassay results, toxicity, cross-reactivity, pharmacokinetics, pharmacodynamics, bioavailability, and solubility. In some embodiments, the generative model comprises a probabilistic autoencoder. In some embodiments, the generative model comprises a variational autoencoder having a probabilistic encoder, a probabilistic decoder, and a sampling module. In some embodiments, the probabilistic encoder is configured to provide an output comprising a pair of a vector of means and a vector of standard deviations. In some embodiments, the sampling module is configured to receive the output of the probabilistic encoder and define a latent variable based on the output of the encoder, and generate one or more latent representations, wherein the latent variable is modeled by a probability distribution. In some embodiments, the probabilistic decoder is configured to decode latent representations and generate random variables over values of fingerprint elements. In some embodiments, the probability distribution is selected from the group consisting of Normal distribution, Laplace distribution, Elliptical distribution, Student's t distribution, Logistic distribution, Uniform distribution, Triangular distribution, Exponential distribution, Invertible cumulative distribution, Cauchy distribution, Rayleigh distribution, Pareto distribution, Weibull distribution, Reciprocal distribution, Gompertz distribution, Gumbel distribution, Erlang distribution, Logarithmic Normal distribution, Gamma distribution, Dirichlet distribution, Beta distribution, Chi-Squared distribution, F distribution, and variations thereof. In some embodiments, the probabilistic encoder and the probabilistic decoder are trained concurrently. In some embodiments, the computer system comprises a GNU. In some embodiments, the generative model further comprises a predictor. In some embodiments, the predictor is configured to predict the values of one or more label elements for at least a subset of the fingerprint associated training labels. In some embodiments, the machine learning network is configured to provide an output comprising a system-generated chemical compound fingerprint that is not in the training data set.

In a further aspect, the methods and systems described herein relate to a method for drug prediction. The method may comprise training a generative model with a training data set comprising chemical compound fingerprints and associated training labels comprising one or more label elements having empirical or predicted label element values. In some embodiments, the labels comprise one or more elements selected from the group consisting of bioassay results, toxicity, cross-reactivity, pharmacokinetics, pharmacodynamics, bioavailability, and solubility. In some embodiments, the generative model comprises a probabilistic autoencoder. In some embodiments, the generative model comprises a variational autoencoder comprising a probabilistic encoder and a probabilistic decoder and a sampling module. In some embodiments, the method further comprises providing from the encoder an output comprising a pair of vector of means and vector of standard deviations for each chemical compound fingerprint in the training data set. In some embodiments, the probabilistic encoder and probabilistic decoder are trained concurrently. In some embodiments, training comprises training the probabilistic encoder to encode a chemical compound fingerprint as a vector of means and a vector of standard deviations defining a latent variable, drawing from the latent variable a latent representation, and training the probabilistic decoder to decode the latent representation as a probabilistic reconstruction of the chemical compound fingerprint. In some embodiments, the latent variable is modeled by a probability distribution selected from the group consisting of Normal distribution, Laplace distribution, Elliptical distribution, Student's t distribution, Logistic distribution, Uniform distribution, Triangular distribution, Exponential distribution, Invertible cumulative distribution, Cauchy distribution, Rayleigh distribution, Pareto distribution, Weibull distribution, Reciprocal distribution, Gompertz distribution, Gumbel distribution, Erlang distribution, Logarithmic Normal distribution, Gamma distribution, Dirichlet distribution, Beta distribution, Chi-Squared distribution, F distribution, and variations thereof. In some embodiments, training comprises optimizing a variational lower bound for the variational autoencoder using backpropagation. In some embodiments, the generative model resides in a computer system having a GNU. In some embodiments, the generative model comprises a predictor module. In some embodiments, the method further comprises predicting one or more values for label elements associated with one or more chemical compound fingerprints in the training data set. In some embodiments, the method further comprises generating from the generative model an output comprising identifying information for a chemical compound not represented in the training set.

In a yet further aspect, the methods and systems described herein relate to a computer system for generation of chemical compound representations. The system may comprise a probabilistic autoencoder. The system may be trained by inputting a training data set comprising chemical compound fingerprints and associated training labels comprising one or more label elements and generating reconstructions of chemical compound fingerprints. The system's training may be constrained by a reconstruction error and/or a regularization error. The generated reconstructions may be sampled from a reconstruction distribution. The reconstruction error may comprise the negative likelihood that an input chemical compound fingerprint is drawn from the reconstruction distribution. The system's training may comprise having the probabilistic autoencoder learn to approximate an encoding distribution. The regularization error may comprise a penalty associated with the complexity of the encoding distribution. In some embodiments, the system is configured to generate chemical compound fingerprints that satisfy selected values for one or more label elements. In some embodiments, the training labels do not comprise the selected values for the one or more label elements. In some embodiments, each chemical compound fingerprint uniquely identifies a chemical compound. In some embodiments, the probabilistic autoencoder comprises at least 2, 3, 4, 5, 6, 7, 8, 9, 10, 11, 12, 13, 14, 15, 16, 17, 18, 19, 20, or more layers. In some embodiments, the computer system may further comprise a predictor configured to predict a value for one or more label elements associated with one or more chemical compound fingerprints in the training data set. In some embodiments, the label elements comprise one or more elements selected from the group consisting of bioassay results, toxicity, cross-reactivity, pharmacokinetics, pharmacodynamics, bioavailability, and solubility.

In yet another aspect, the methods and systems described herein relate to a method for generation of chemical compound representations. The method may comprise training a machine learning model. The training may comprise inputting to the machine learning model chemical compound fingerprints and associated labels comprising one or more label elements, and generating reconstructions of chemical compound fingerprints. The machine learning model may comprise a probabilistic or variational autoencoder. In some embodiments, the training is constrained by a reconstruction error and a regularization error. The generated reconstructions may be sampled from a reconstruction distribution. In some embodiments, the reconstruction error comprises the negative likelihood that an input chemical compound fingerprint is drawn from the reconstruction distribution. The training may comprise having the probabilistic autoencoder learn to approximate an encoding distribution. The regularization error may comprise a penalty associated with the complexity of the encoding distribution.

In a further aspect, the methods and systems described herein relate to a computer system for drug prediction. The system may comprise a machine learning model comprising a generative model. The machine learning model may be trained with a first training data set comprising chemical fingerprint data and an associated set of labels having a first label element and a second training data set comprising chemical fingerprint data and an associated set of labels having a second label element. In some embodiments, the chemical fingerprint data of the first and second training data sets are entered into the units of at least two layers of the generative network. In some embodiments, the labels having the first label element and the labels having the second label element are introduced into different portions of the generative network during training. In some embodiments, the first label element represents the activity of a chemical compound associated with a chemical fingerprint in a first bioassay. In some embodiments, the second label element represents the activity of a chemical compound associated with a chemical fingerprint in a second bioassay. In some embodiments, the system is configured to generate a representation of a chemical compound having a high likelihood of meeting a requirement related to a specified value for the first label element having a first type and a requirement related to a specified value for the second label element. In some embodiments, the high likelihood is greater than 1, 2, 3, 4, 5, 6, 7, 8, 9, 10, 12, 15, 20, 25, 30, 40, 50, 60, 70, 80, 90, 95, 98, 99%, or more. In some embodiments, the requirement related to the specified value for the first label element comprises having a positive result for a first bioassay that is at least 1, 2, 3, 4, 5, 6, 7, 8, 9, 10, 12, 15, 20, 30, 50, 100, 500, 1,000, or more standard deviation over noise. In some embodiments, the requirement related to the specified value for the first label element comprises having a positive result for a first bioassay that is at least 10, 20, 30, 40, 50, 100, 200, 500, 1,000% greater than the activity of a known chemical compound of equal molarity. In some embodiments, the requirement related to the specified value for the first label element comprises having a positive result for a first bioassay that is at least 100% greater than the activity of a known chemical compound of equal molarity. In some embodiments, the requirement related to the specified value for the first label element comprises having a positive result for a first bioassay that is at least 2×, 3×, 4×, 5×, 6×, 7×, 8×, 9×, 10×, 15×, 25×, 50×, 100×, 200×, 300×, 400×, 500×, 1,000×, 10,000×, or 10,0000× greater than the activity of a known chemical compound of equal molarity. In some embodiments, the requirement related to the specified value for the second label element comprises having a positive result for a second bioassay that is at least 1, 2, 3, 4, 5, 6, 7, 8, 9, 10, 12, 15, 20, 30, 50, 100, 500, 1,000, or more standard deviation over noise. In some embodiments, the requirement related to the specified value for the second label element comprises having a positive result for a second bioassay that is at least 10, 20, 30, 40, 50, 100, 200, 500, or 1,000% greater than the activity of a known chemical compound of equal molarity. In some embodiments, the requirement related to the specified value of the second label element comprises having a positive result for a second bioassay that is at least 2×, 3×, 4×, 5×, 6×, 7×, 8×, 9×, 10×, 15×, 25×, 50×, 100×, 200×, 300×, 400×, 500×, 1,000×, 10,000×, or 10,0000× greater than the activity of a known chemical compound of equal molarity.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
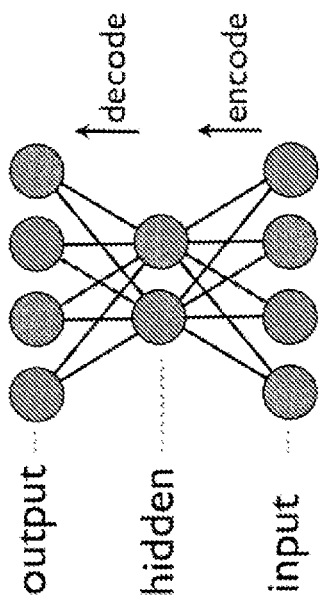
FIG. 1 shows an illustrative depiction of an autoencoder.

The present invention, in various embodiments, relates to methods and systems that enable direct generation of chemical compound candidate representations by the use of machine learning and/or artificial intelligence methods. In various embodiments, the methods and systems described herein relate to utilizing generative models, deep generative models, directed graphical models, deep directed graphical models, directed latent graphical models, latent variable generative models, nonlinear Gaussian belief networks, sigmoid belief networks, deep autoregressive networks, neural autoregressive distribution estimators, generalized denoising autoencoders, deep latent Gaussian models, and/or combinations thereof. In some embodiments, generative models utilize a probabilistic autoencoder, such as a variational autoencoder. The components of the generative model, such as a variational autoencoder, may comprise multi-layer perceptrons implementing a probabilistic encoder and a probabilistic decoder. The encoder and decoder may be trained simultaneously, for example by using backpropagation. The systems and methods described herein may be used to generate novel chemical compounds that were not included in the training data set used to train the generative model. Further, the methods and systems of the invention in various embodiments increase likelihood of identifying one or more chemical compounds with a desired set of properties. In various embodiments, the methods and systems of the invention comprise simultaneous prediction of effects and side effects of a chemical compound, or finding a new use for an existing drug, commonly referred to as drug repositioning. In various embodiments, references to "compound" or "generating a compound" relate to uniquely identifying information about the compound and generation thereof, but not necessarily a physical production of the compound. Such uniquely identifying information may comprise a chemical formula or structure, a reference code, or any other suitable identifier described herein or otherwise known in the art.

In exemplary embodiments, the desired set of properties for a chemical compound comprises one or more of activity, solubility, toxicity, and ease of synthesis. The methods and systems described herein may facilitate prediction of off-target effects or prediction of how drug candidates interact with targets other than a selected target.

While machine learning approaches have been successful in computerized image recognition, the improvements it has thus far offered in the field of computerized drug discovery have been modest in comparison. The systems and methods described herein provide a solution involving generative models that improves predictions regarding chemical compounds and their activities, effects, side effects, and properties in a novel way. The generative models described herein provide a unique approach by generating compounds according to desired specifications.

In various embodiments, the methods and systems described herein are provided with compound information typically characterized by a set of molecular descriptors, representing chemical information, such as a chemical formula, chemical structure, electron density or other chemical characteristics. Compound information may comprise fingerprint representations of each compound. Further, the methods and systems described herein may be provided with labels comprising additional information, including biological data, for example bioassay results, such as those that depict activities of a compound with respect to particular targets, such as receptors or enzymes. The methods and systems described herein may be trained with a training set comprising pairs of a vector of values of molecular descriptors and a vector of label element values. The compound information and labels in combination typically comprise data on the compound's biological and chemical characteristics, comprising, for example, bioassay data, solubility, cross-reactivity, as well as other chemical features such as hydrophobicity, phase transition boundaries, such as freezing point, or any other information that can be used to characterize the structure or function of the compound. Upon training, the systems and methods described herein may output chemical information identifying one or more compounds, such as one or more chemical fingerprints. In some embodiments, the methods and systems described herein may output identifying chemical information for one or more compounds that are expected to have desired chemical and/or biological characteristics. For example, identified compounds may be expected to have test outcomes within a desired range for one or more specified bioassay results, toxicity, cross-reactivity, etc. The methods and systems described herein may in some cases output a list of compounds ranked according to the level of expectation of having the desired characteristics. The identified compounds may be used as lead compounds or initial compounds in a hit-lead study.

The methods and systems described herein may utilize chemical compounds of a certain size. For example, the generative models, for example deep generative models, in various embodiments, may be trained with and/or may generate representations of compounds with a molecular weight that is less than 100,000, 50,000, 40,000, 30,000, 20,000, 15,000, 10,000, 9,000, 8,000, 7,000, 6,000, 5,000, 4,000, 3,000, 2,500, 2,000, 1,500, 1,250, 1,000, 900, 800, 750, 600, 500, 400, 300 Daltons or less.

Some portions of the detailed descriptions that follow are presented in terms of algorithms and symbolic representations of operations on data bits within a computer memory. These descriptions and representations are the means used by those skilled in the data processing arts to most effectively convey the substance of their work to others skilled in the art.

All of these and similar terms are to be associated with the appropriate physical quantities and are merely convenient labels applied to these quantities. Unless specifically stated otherwise as apparent from the following discussion, it is appreciated that throughout the description, discussions utilizing terms such as "processing" or "computing" or "calculating" or "determining" or "displaying" or the like, refer to the action and processes of a computer system, or similar electronic computing device that manipulates and transforms data represented as physical (electronic) quantities within the computer system's registers and memories into other data similarly represented as physical quantities within the computer system's memories or registers or other such information storage, transmission, or display devices.

The systems and methods of the invention may comprise one or more machine learning structures and substructures, such as a generative model, a probabilistic autoencoder, or a variational autoencoder implemented in a multi-layer perceptron, and may utilize any suitable learning algorithm described herein or otherwise known in the art, for example, without limitation, backpropagation with stochastic gradient descent to minimize a loss function, or backpropagation with stochastic gradient ascent to optimize a variational lower bound. Once the model is trained, it can be used to evaluate new instances of data that are presented to a computer or computer network for prediction, for example with the use of a prediction module (or predictor). The prediction module may comprise some or all of the machine learning structures that were used during the training phase. In some embodiments, new chemical compound fingerprints may be generated by sampling from a random variable generated by the model.

In several embodiments, the methods and systems described herein train a probabilistic or variational autoencoder that can then be used as a generative model. In one embodiment, the probabilistic or variational autoencoder is embodied as a multi-layer perceptron comprising at least 1, 2, 3, 4, 5, 6, 7, 8, 9, 10, 11, 12, or more hidden layers. In some cases, the probabilistic or variational autoencoder may comprise a multi-layer perceptron, comprising a probabilistic encoder and a probabilistic decoder. In other embodiments, any of a variety of statistical models that can be trained to form a generative model as described in further detail elsewhere herein may be implemented. Supervised or semi-supervised training algorithms may be used to train the machine learning system with the specified architecture.

In a first aspect, the methods and systems described herein relate to a computer system for generation of representations of chemical compounds. The system may comprise a probabilistic or variational autoencoder. The probabilistic or variational autoencoder may comprise a probabilistic encoder for converting fingerprint data into a latent random variable from which a latent representation may be sampled, and a probabilistic decoder for converting a latent representation to a random variable from which a sample may be drawn, thereby reconstructing a chemical compound fingerprint, and a sampling module that can sample a latent representation from the latent random variable and/or a sampling module that can sample a chemical compound fingerprint from the random variable. The system may be trained by inputting representations of chemical compounds and their associated labels, and generating reconstructions of chemical compound representations wherein the chemical compound fingerprints and the distributions of reconstruction differ by the value of a loss function comprising a reconstruction error and a regularization error. The reconstruction error may comprise the negative likelihood that an input chemical compound representation is drawn from the random variable generated by the probabilistic decoder. The probabilistic autoencoder may be trained to learn to approximate an encoding distribution. The regularization error may comprise a penalty associated with the complexity of the encoding distribution. The system may be trained to optimize, for example to minimize, the loss function. In some embodiments, the system is trained by further inputting training labels associated with the chemical compounds. In some embodiments, the system is configured to generate chemical compound fingerprints that have a high likelihood of satisfying a selected set of desired label element values. In some embodiments, the set of desired label element values does not appear in a label in the training data set. In some embodiments, each chemical compound fingerprint uniquely identifies a chemical compound. In some embodiments, the encoder is configured to provide an output comprising a pair of a vector of means and a vector of standard deviations. The system may define a latent random variable based on the output of the encoder. The latent random variable may be modeled by a probability distribution, for example a Normal distribution, Laplace distribution, Elliptical distribution, Student's t distribution, Logistic distribution, Uniform distribution, Triangular distribution, Exponential distribution, Invertible cumulative distribution, Cauchy distribution, Rayleigh distribution, Pareto distribution, Weibull distribution, Reciprocal distribution, Gompertz distribution, Gumbel distribution, Erlang distribution, Logarithmic Normal distribution, Gamma distribution, Dirichlet distribution, Beta distribution, Chi-Squared distribution, or F distribution, or variations thereof. The encoder and/or the decoder may comprise one or more layers of a multi-layer perceptron or other type of neural network, such as a recurrent neural network. The system may further comprise a predictor for predicting label element values associated with a chemical compound fingerprint. In some embodiments, the label elements comprise one or more elements selected from the group consisting of bioassay results, toxicity, cross-reactivity, pharmacokinetics, pharmacodynamics, bioavailability, and solubility.

In another aspect, the systems and methods described herein relate to a method for generation of chemical compound representations. The method may comprise training a generative model. The training may comprise (1) inputting representations of chemical compounds and their associated labels, and (2) generating reconstructions of chemical compound fingerprints. The generative model may comprise a probabilistic or variational autoencoder comprising a) a probabilistic encoder for encoding fingerprint and label data as a latent variable from which a latent representation may be sampled; b) a probabilistic decoder for converting latent representations to random variables from which reconstructions of the fingerprint data may be sampled; and c) a sampling module for sampling a latent variable to generate a latent representation, or sampling a random variable to generate a fingerprint reconstruction. The system may be trained to optimize, for example to minimize, the loss function comprising a reconstruction error and a regularization error. The reconstruction error may comprise the negative likelihood that an encoded chemical compound representation is drawn from the random variable output by the probabilistic decoder. The training may comprise having the variational or probabilistic autoencoder learn to approximate an encoding distribution. The regularization error may comprise a penalty associated with the complexity of the encoding distribution.

In yet another aspect, the methods and systems described herein relate to a computer system for drug prediction. It is understood that "drug prediction" as it relates to various embodiments of the invention, refers to an analysis for chemical compounds to have certain chemical and physical properties. Subsequent activities, such as synthesis, in vivo and in vitro testing, and clinical trials with a chemical compound are understood to follow in certain embodiments of the invention, however, such subsequent activities are not implied in the term "drug prediction." The system may comprise a machine learning model comprising a generative model. The generative model may be trained with a training data set comprising chemical compound representations such as fingerprint data. In some embodiments, the machine learning model comprises at least 2, 3, 4, 5, 6, 7, 8, 9, 10, or more layers of units. In some embodiments, the training data set further comprises labels associated with at least a subset of the chemical compounds in the training data set. The labels may have label elements such as one or more of compound activities and properties such as bioassay results, toxicity, cross-reactivity, pharmacokinetics, pharmacodynamics, bioavailability, solubility or any other suitable label element known in the art. The generative model may comprise a probabilistic autoencoder. In some embodiments, the probabilistic autoencoder comprises a multi-layer perceptron with at least 3, 4, 5, 6, 7, 8, 9, 10, 11, 12, 13, 14 or more layers of units. In some embodiments, the generative model comprises a probabilistic or variational autoencoder that comprises a probabilistic encoder, a probabilistic decoder, and a sampling module. The probabilistic encoder may be configured to provide an output comprising a pair of a vector of means and a vector of standard deviations. The system may define a latent random variable based on the output of the encoder. The latent random variable may be modeled by a probability distribution, for example a Normal distribution, Laplace distribution, Elliptical distribution, Student's t distribution, Logistic distribution, Uniform distribution, Triangular distribution, Exponential distribution, Invertible cumulative distribution, Cauchy distribution, Rayleigh distribution, Pareto distribution, Weibull distribution, Reciprocal distribution, Gompertz distribution, Gumbel distribution, Erlang distribution, Logarithmic Normal distribution, Gamma distribution, Dirichlet distribution, Beta distribution, Chi-Squared distribution, F distribution, or variations thereof. The computer system may comprise a GNU. The generative model may further comprise a predictor. The predictor may be configured to predict label element values for at least a subset of the compound fingerprints in the training data set. In some embodiments, the generative model is configured to provide an output comprising a chemical compound representation that was generated by the model. The representation may be sufficient to uniquely identify the chemical compound. The generated chemical compound may be a compound that was not included in the training data set, and in some cases, it may be a compound that has never been synthesized or even conceived.

In a further aspect, the methods and systems described herein relate to a method for drug prediction. The method may comprise training a machine learning model with a training data set comprising chemical compound representations and associated label element values representing the compound's activities or properties for at least a subset of the chemical compounds in the training data set. The machine learning model may comprise a generative model. In some embodiments, the labels have elements such as bioassay results, toxicity, cross-reactivity, pharmacokinetics, pharmacodynamics, bio availability, or solubility. The generative model may comprise a probabilistic autoencoder, such as a probabilistic or variational autoencoder. The probabilistic or variational autoencoder may comprise a probabilistic encoder, a probabilistic decoder, and a sampling module. The method may further comprise providing from the encoder an output comprising a pair of a vector of means and vector of standard deviations. The pair of the vector of means and vector of standard deviations may be used to define a latent variable. In some embodiments, the method further comprises having the sampling module draw latent representations from the latent variable. The latent variable may be modeled by a probability distribution such as Normal distribution, Laplace distribution, Elliptical distribution, Student's t distribution, Logistic distribution, Uniform distribution, Triangular distribution, Exponential distribution, Invertible cumulative distribution, Cauchy distribution, Rayleigh distribution, Pareto distribution, Weibull distribution, Reciprocal distribution, Gompertz distribution, Gumbel distribution, Erlang distribution, Logarithmic Normal distribution, Gamma distribution, Dirichlet distribution, Beta distribution, Chi-Squared distribution, F distribution, or variations thereof. In some embodiments, the machine learning model resides in a computer system having a GPU. In some embodiments, the machine learning model comprises a predictor module. The method may further comprise predicting label element values for a subset of the training data using the predictor module. In some embodiments, the method further comprises generating from the machine learning model an output comprising a set of molecular descriptors sufficient for identifying a chemical compound. The chemical compound may be absent from the training set.

In a yet further aspect, the methods and systems described herein relate to a computer system for generation of chemical compound representations. The system may comprise a probabilistic or variational autoencoder, wherein the system is trained by inputting chemical compound representations and generating reconstructions of chemical compound representations, wherein the system's training is constrained by a reconstruction error and/or a regularization error. The generated reconstructions may be sampled from a reconstruction distribution and the reconstruction error may comprise the negative likelihood that an input chemical compound fingerprint is drawn from the reconstruction distribution. The regularization error may comprise a penalty associated with the complexity of the encoding distribution. Label element values associated with the chemical compounds may be input to the system at the same point as chemical compound representations or at another point, for example labels may be input to the decoder of an autoencoder. In some embodiments, the system is configured to generate chemical compound representations where the chemical compounds carry a high likelihood of satisfying one or more requirements defined by a set of desired label element values. In some embodiments, the set of desired label element values may not have been part of the training data set. In some embodiments, each chemical compound fingerprint uniquely identifies a chemical compound. In some embodiments, the training further constrains the total information flow through a layer of the generative network. In some embodiments, the probabilistic or variational autoencoder comprises a multi-layer perceptron with at least 2, 3, 4, 5, 6, 7, 8, 9, 10, or more layers. In some embodiments, the system further comprises a predictor for associating labels to chemical compound representations. In some embodiments, the labels comprise one or more label elements, such as, bioassay results, toxicity, cross-reactivity, pharmacokinetics, pharmacodynamics, bioavailability, and solubility.

In yet another aspect, the methods and systems described herein relate to a method for generation of chemical compound representations. The method may comprise training a machine learning model. The training may comprise (1) inputting to the machine learning model chemical compound representations, such as fingerprints, and (2) generating reconstructions of chemical compound representations, e.g. fingerprints. The machine learning model may comprise a probabilistic or variational autoencoder. The system may be trained to optimize, for example to minimize, a loss function comprising a reconstruction error and a regularization error. The generated reconstructions may be sampled from a reconstruction distribution. The reconstruction error may comprise the negative likelihood that an input chemical compound fingerprint is drawn from the reconstruction distribution. The training may comprise having the probabilistic or variational autoencoder learn to approximate an encoding distribution. The regularization error may comprise a penalty associated with the complexity of the encoding distribution.

In a further aspect, the methods and systems described herein relate to a computer system for drug prediction. The system may comprise a machine learning model comprising a generative model. The machine learning model may be trained with a first training data set comprising chemical compound representations, such as fingerprints, and an associated set of labels having values for a first label element and a second training data set comprising chemical compound representations, such as fingerprints, and an associated set of labels having values for a second label element. In some embodiments, the labels having a first label element and the labels having a second label element are introduced into different portions of the generative model during training, for example into the encoder and decoder, respectively. In some embodiments, labels having a first label element represent the activity of a chemical compound in a first bioassay. In some embodiments, labels having a second label element represent the activity of a chemical compound in a second bioassay. In some embodiments, the system is configured to generate a representation of a chemical compound having a high likelihood of meeting a requirement related to a label having a first label element value and a requirement related to a label having a second label element value. In some embodiments, the high likelihood is greater than 1, 2, 3, 4, 5, 6, 7, 8, 9, 10, 12, 15, 20, 25, 30, 40, 50, 60, 70, 80, 90, 95, 98, 99%, or more. In some embodiments, the requirement related to the first label element comprises having a positive result for a first bioassay that is at least 1, 2, 3, 4, 5, 6, 7, 8, 9, 10, 12, 15, 20, 30, 50, 100, 500, 1,000, or more standard deviations over noise. In some embodiments, the requirement related to the first label element comprises having a positive result for a first bioassay that is at least 10, 20, 30, 40, 50, 100, 200, 500, 1,000%, or more compared to the activity of a known chemical compound of equal molarity. In some embodiments, the requirement related to the second label element comprises having a positive result for a second bioassay that is at least 1, 2, 3, 4, 5, 6, 7, 8, 9, 10, 12, 15, 20, 30, 50, 100, 500, 1,000, or more standard deviations over noise. In some embodiments, the requirement related to the second label element comprises having a positive result for a second bioassay that is at least 10, 20, 30, 40, 50, 100, 200, 500, 1,000% greater than the activity of a known chemical compound of equal molarity.

Generative Model

In various embodiments, the systems and methods described here utilize a generative model as the core component.

Generative models, according to the methods and systems of the invention, can be used to randomly generate observable-data values given values of one or more hidden parameters. Generative models can be used for modeling data directly (i.e., modeling chemical compound observations drawn from a probability density function) or as an intermediate step to forming a conditional probability density function. Examples of generative models include, but are not limited to probabilistic autoencoders, variational autoencoders, Gaussian mixture models, hidden Markov models, and restricted Boltzmann machines. Generative models described in further detail elsewhere herein typically specify a joint probability distribution over chemical compound representations, i.e., fingerprints, and labels associated with the compounds.

As an example, a set of chemical compounds may be represented as $x=x_1, x_2, \ldots, x_N$, where $x_i$ may comprise a fingerprint representation of a compound and N is the number of compounds in the set. These compounds may be associated with a set of N labels $L=(l_1, l_2, \ldots, l_N)$, where $l_i$ is a label that may comprise, for example, values for label elements such as compound activity, toxicity, solubility, ease of synthesis, or other outcomes in bioassay results or predictive studies. A generative model may be built upon the assumption that these chemical compounds and their associated labels are generated from some unknown distribution D, i.e. $D \sim (x_n, l_n)$. Training a generative model may utilize a training methodology that adjusts the model's internal parameters such that it models the joint probability distribution $p(x, l)$ given the data examples in the training data set. After a generative model has been trained, it may be used to generate values of x conditioned on values of l, i.e., $x \sim p(x|l)$. For example, a generative model trained on a training set of fingerprints and labels may generate a representation of a chemical compound that has a high likelihood of meeting the requirements of a specified label value.

Autoencoders and variations thereof (collectively referred to as "autoencoders") can be used as building blocks in the methods and systems described herein. Autoencoders, such as probabilistic autoencoders and variational autoencoders, provide examples of generative models. In various implementations, autoencoders may be used to implement directed graphical models, which are distinct from undirected graphical models such as restricted Boltzmann machines.

In various embodiments, autoencoders described herein comprise two serialized components, namely, an encoder and a decoder. The encoder can encode an input data point as a latent variable from which a latent representation may be sampled. The decoder in turn can decode a latent representation to generate a random variable from which a reconstruction of the original input may be sampled. The random variable may be modeled by a probability distribution, for example a Normal distribution, Laplace distribution, Elliptical distribution, Student's t distribution, Logistic distribution, Uniform distribution, Triangular distribution, Exponential distribution, Invertible cumulative distribution, Cauchy distribution, Rayleigh distribution, Pareto distribution, Weibull distribution, Reciprocal distribution, Gompertz distribution, Gumbel distribution, Erlang distribution, Logarithmic Normal distribution, Gamma distribution, Dirichlet distribution, Beta distribution, Chi-Squared distribution, or F distribution, or variations thereof. Typically, the dimensionalities of the input data and the output reconstructions can be the same.

In various embodiments, autoencoders described herein are trained to reproduce their input, for example by minimizing a loss function. A number of training algorithms can be used to optimize, for example to minimize, the reconstruction error and/or regularization error represented by the loss function. Examples of suitable training algorithms are described in further detail elsewhere herein and otherwise known in the art and include, without limitation, backpropagation with stochastic gradient descent. In addition, a number of methods known in the art—such as dropout, sparse architectures, and denoising—may be used to discourage the autoencoder from overfitting to the training data set and simply learning the identity function. As used herein, the term "minimize" may include minimizing the absolute value of a term.

A trained autoencoder, such as a trained probabilistic or variational autoencoder, may be used to generate or simulate observable-data values by sampling from the modeled joint probability distribution to generate a latent representation and by decoding this latent representation to reconstruct an input data point. In one embodiment, the weights of the autoencoder are adjusted during training by an optimization method. In one embodiment, the weights are adjusted by using backpropagation in conjunction with gradient descent to optimize, for example to minimize, the loss function. In one embodiment, individual layers of the autoencoder may be pre-trained and the weights of the entire autoencoder are fine-tuned together.

In various embodiments, the systems and methods described herein may utilize deep network architectures, including but not limited to deep generative models, probabilistic autoencoders, variational autoencoders, directed graphical models, belief networks, or variations thereof.

Figure 2A:
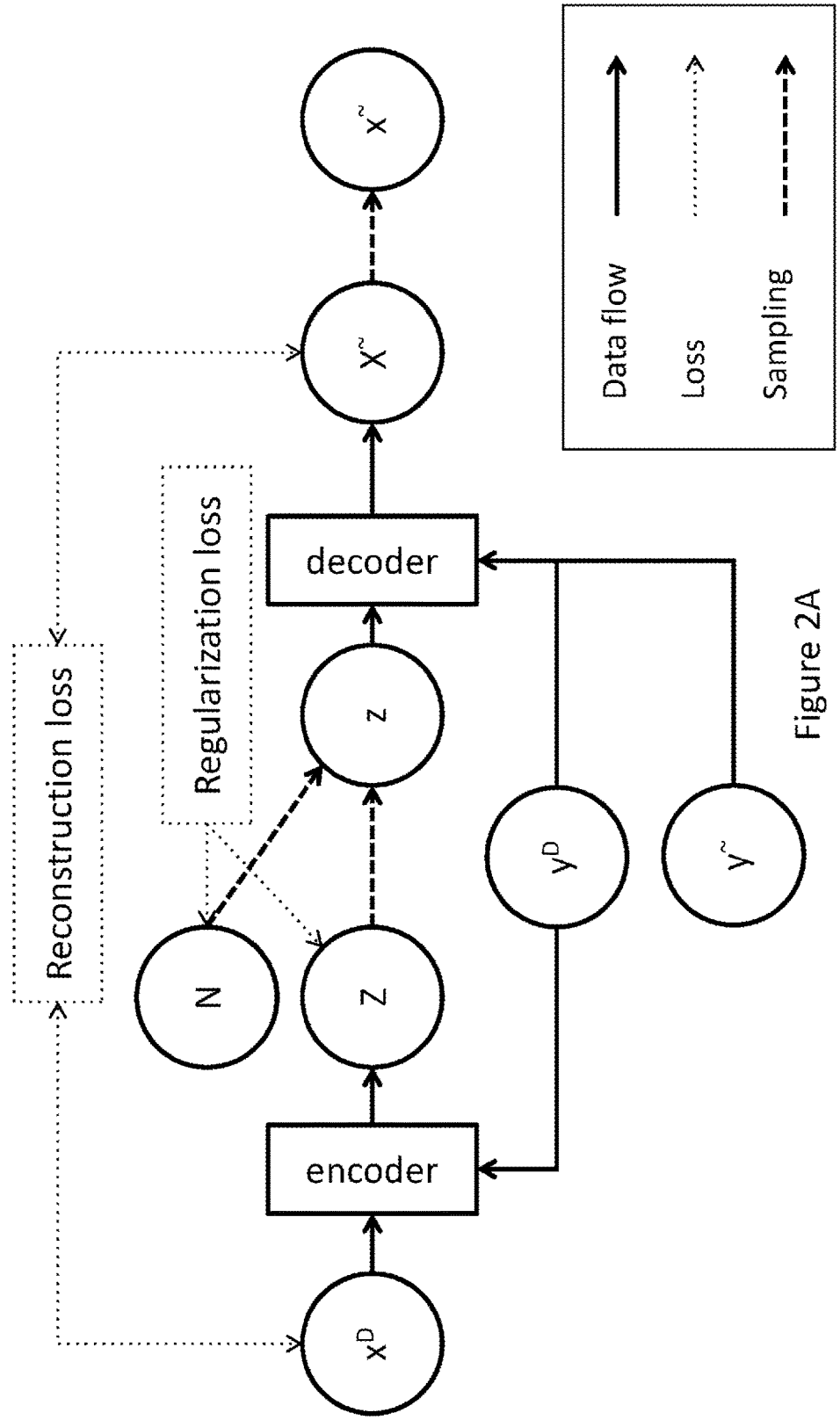
FIG. 2A demonstrates an exemplary architecture of a multi-component generative model without a predictor. A generative model with such architecture may be trained by supervised learning.
Figure 2B:
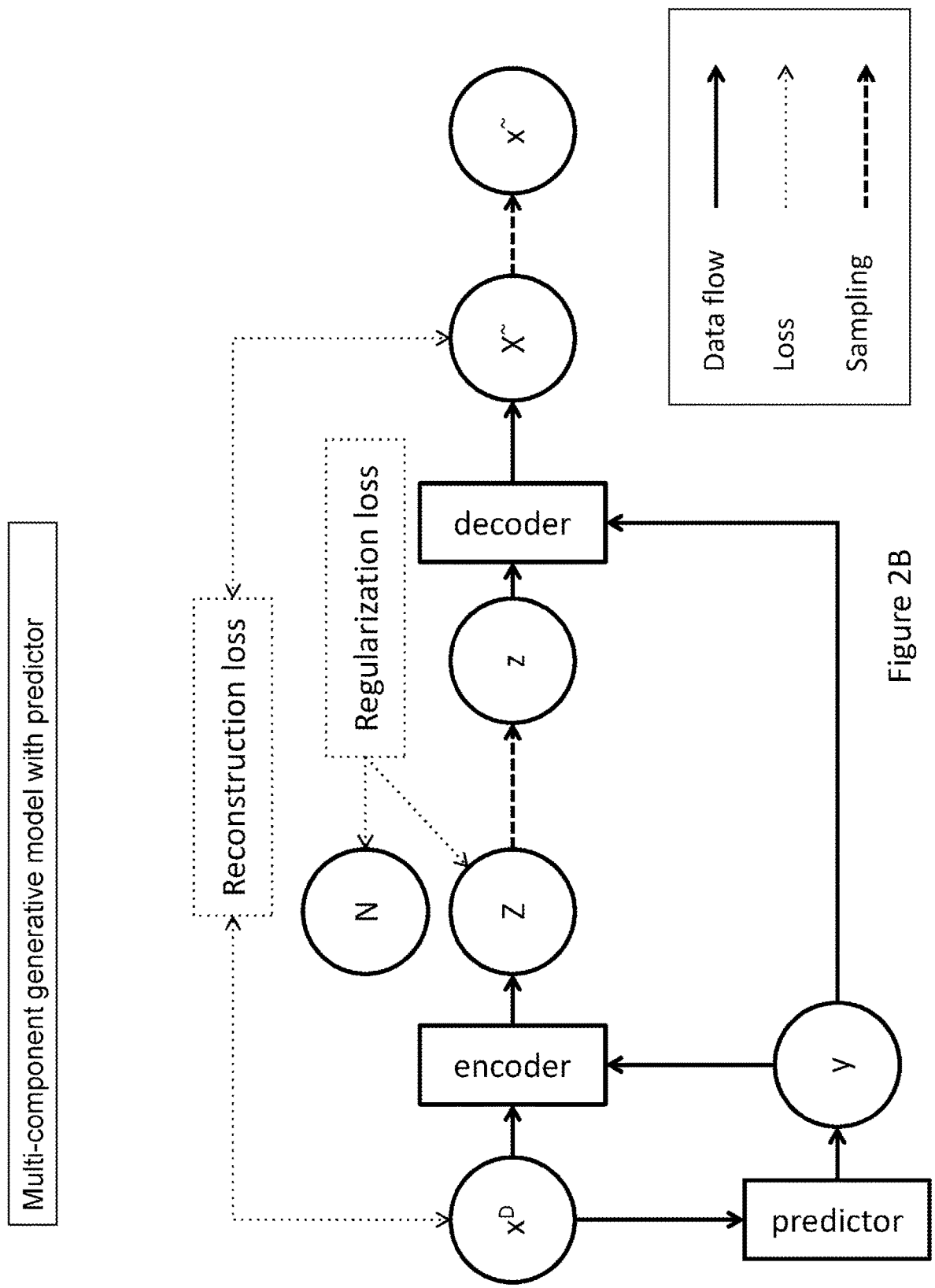
FIG. 2B demonstrates an exemplary architecture of multi-component generative model with a predictor. A generative model with such architecture may be trained by semi-supervised learning.

In various embodiments, generative models described herein comprise probabilistic autoencoders with multiple components. For example, a generative model may have one or more of an encoder, decoder, sampling module, and optional predictor (FIGS. 2A-2B). The encoder may be used to encode representations of chemical compounds, e.g., fingerprints, as an output of a different form, e.g. a latent variable. During training, the encoder must learn an encoding model that specifies a non-linear mapping of input x to latent variable Z. For example, if the latent variable Z has been parameterized as $Z=\mu_z(x)+\sigma_z(x)\epsilon_z$ where $\epsilon_z=N(0,1)$, the encoder may output a pair of a vector of means and a vector of standard deviations. The sampling module may draw a sample from latent variable Z to generate a latent representation, z. During training, the decoder may learn a decoding model that maps latent variable Z to a distribution on x, i.e., the decoder may be used to convert a latent representation and a label into a random variable, X~, from which the sampling module may draw a sample to generate a compound fingerprint, x~. The latent variable or the random variable may be modeled by a suitable probability distribution function, such as the normal distribution, the parameters of which are output by the encoder or the decoder, respectively. The sampling module may sample from any suitable probability distribution, such as the Normal distribution, Laplace distribution, Elliptical distribution, Student's t distribution, Logistic distribution, Uniform distribution, Triangular distribution, Exponential distribution, Invertible cumulative distribution, Cauchy distribution, Rayleigh distribution, Pareto distribution, Weibull distribution, Reciprocal distribution, Gompertz distribution, Gumbel distribution, Erlang distribution, Logarithmic Normal distribution, Gamma distribution, Dirichlet distribution, Beta distribution, Chi-Squared distribution, F distribution, or a variation thereof or a suitable probability distribution function otherwise known in the art. The system may be trained so as to minimize the reconstruction error, which typically represents the negative likelihood that the input compound $x^D$ was drawn from the distributions defined by the random variable generated by the decoder, and/or the regularization error, which typically represents a penalty imposed for model complexity. Without being bound by theory, since the encoding model must approximate the true posterior distribution, p(Z|x), which may be intractable, instead of using a direct learning approach, an inference model may be used. A variational autoencoder may use an inference model $q_\phi(Z|x)$ that learns to approximate the true encoding distribution p(Z|x).

To train the VAE, a variational lower bound may be defined on the data likelihood:

$$\log p_\theta(x) = \mathcal{L}(\theta, \phi, x)$$

where $\phi$ denotes the encoding parameters and $\theta$ denotes the decoding parameters. From this definition, it follows that:

$$\mathcal{L}(\theta,\phi,x) = -D_{KL}(q_\phi(Z|x) \| p_\theta(Z)) + E_{q_\phi(Z|x)}[\log p_\theta(x|Z)]$$

Figure 5B:
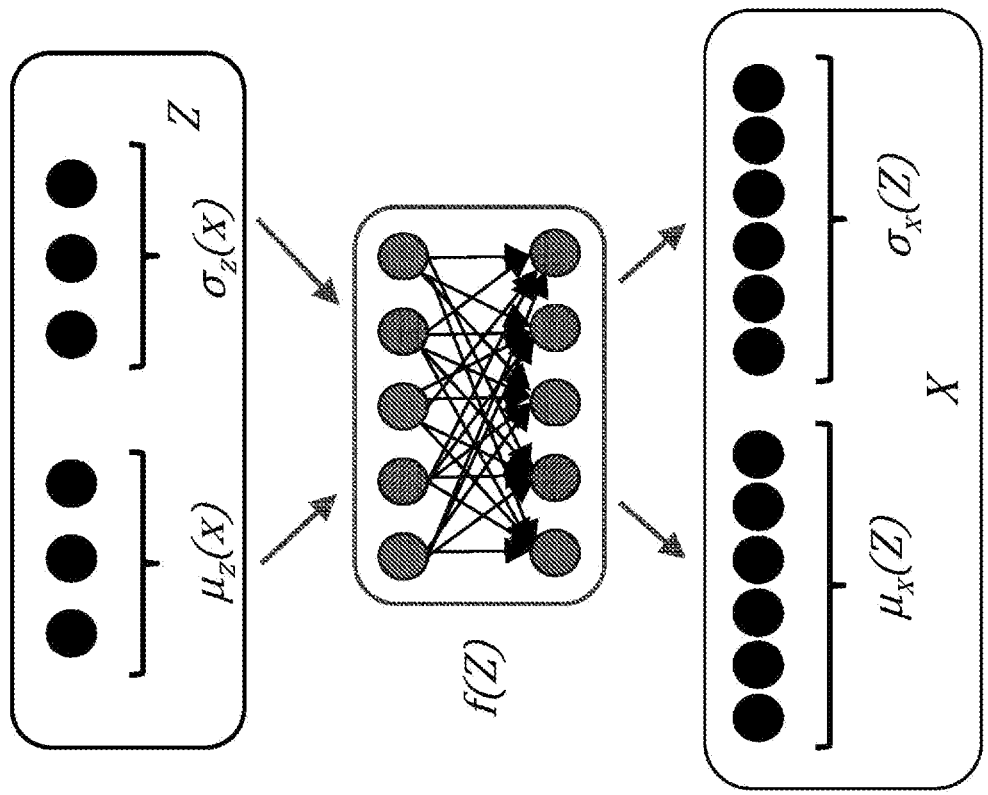
FIG. 5B depicts an illustrative example for a decoder according to various embodiments of the invention.
Figure 5A:
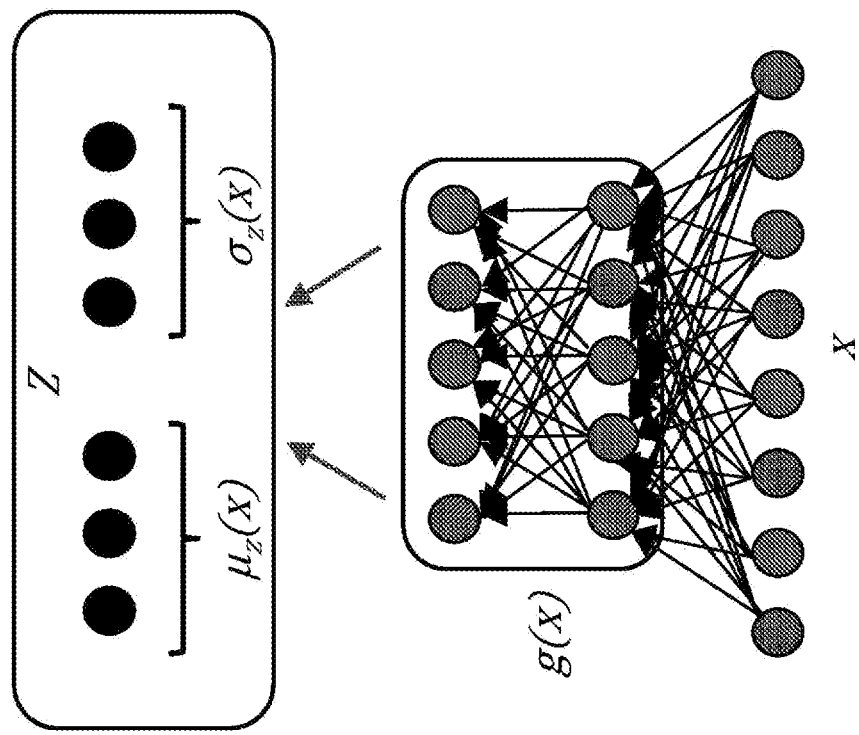
FIG. 5A depicts an illustrative example for an encoder according to various embodiments of the invention.

The first right-hand side (RHS) term, the Kullback-Leibler (KL) divergence of the approximate encoding model from the prior over the latent variable Z, can act as the regularization term. The second RHS term is typically referred to as the reconstruction term. The training process may optimize $\mathcal{L}(\theta, \phi, x)$ with respect to both the encoding parameters $\phi$ and the decoding parameters $\theta$. The inference model (encoder) $q_\phi(Z|x)$ may be parametrized as a neural network:

$$q_\phi(Z|x) = q(Z; g(x,\phi))$$

where g(x) is a function that maps input x to latent variable Z, which is parametrized as $Z=\mu_z(x)+\sigma_z(x)\epsilon_z$ where $\epsilon_z=N(0,1)$, (FIG. 5A). The generative model (decoder) may be similarly parameterized as a neural network:

$$p_\theta(x|Z) = p(x; f(Z,\theta))$$

where f(Z) is a function that maps latent variable Z to a distribution over x, (FIG. 5B). The output of the decoder, X may be parameterized as $$X = \mu_x(Z) + \sigma_x(Z)\epsilon_x, \text{ where } \epsilon_x = N(0,1).$$

Figure 6:
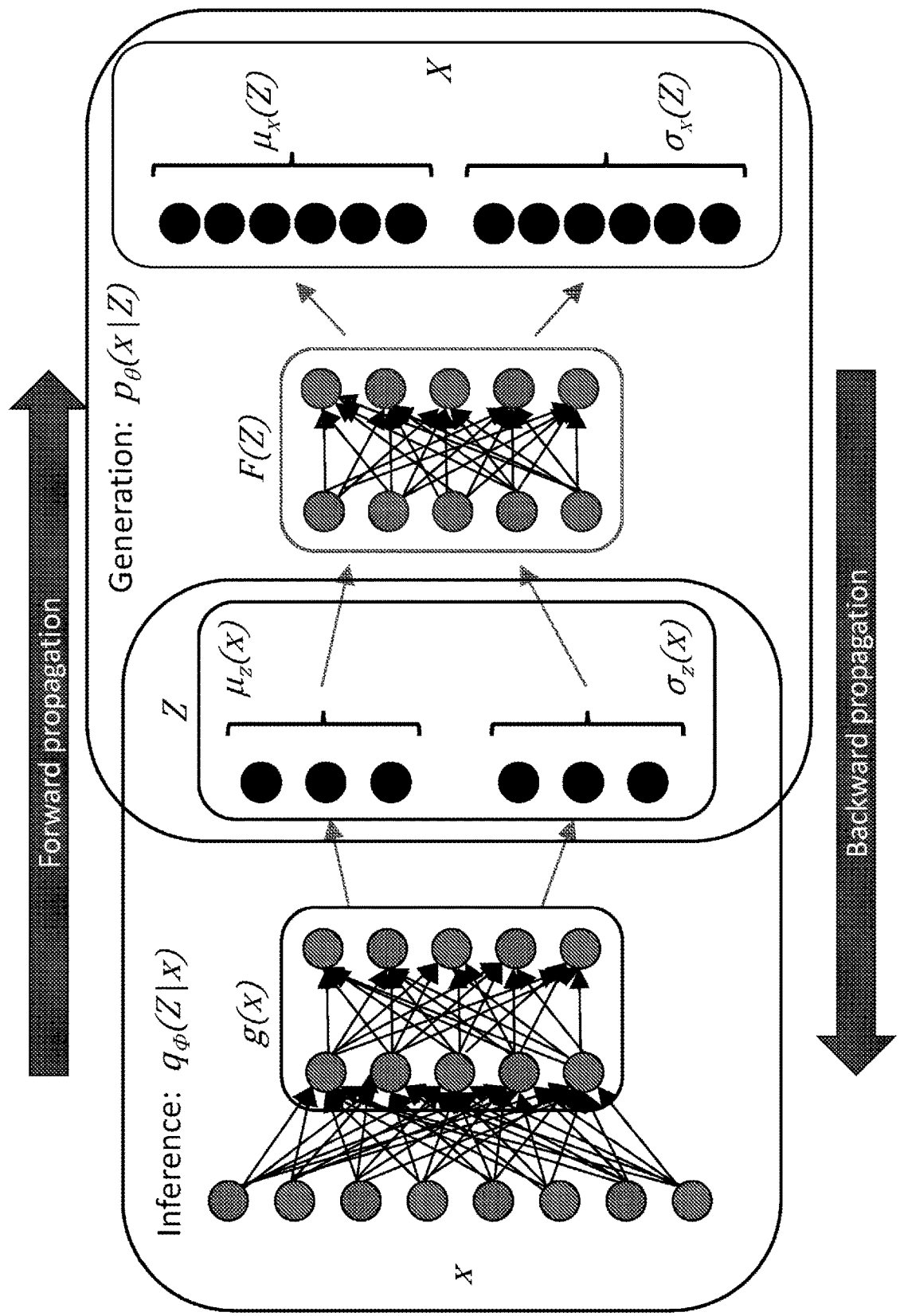
FIG. 6 depicts an illustrative example of a training method of a variational autoencoder according to various embodiments of the invention.

The inference model and generative model may be trained simultaneously by optimizing the variational lower bound using backpropagation with gradient ascent (FIG. 6). Optimization of the variational lower bound may serve to minimize a loss function comprising both the reconstruction error and the regularization error. In some cases, the loss function is or comprises the sum of the reconstruction error and the regularization error.

Figure 17A:
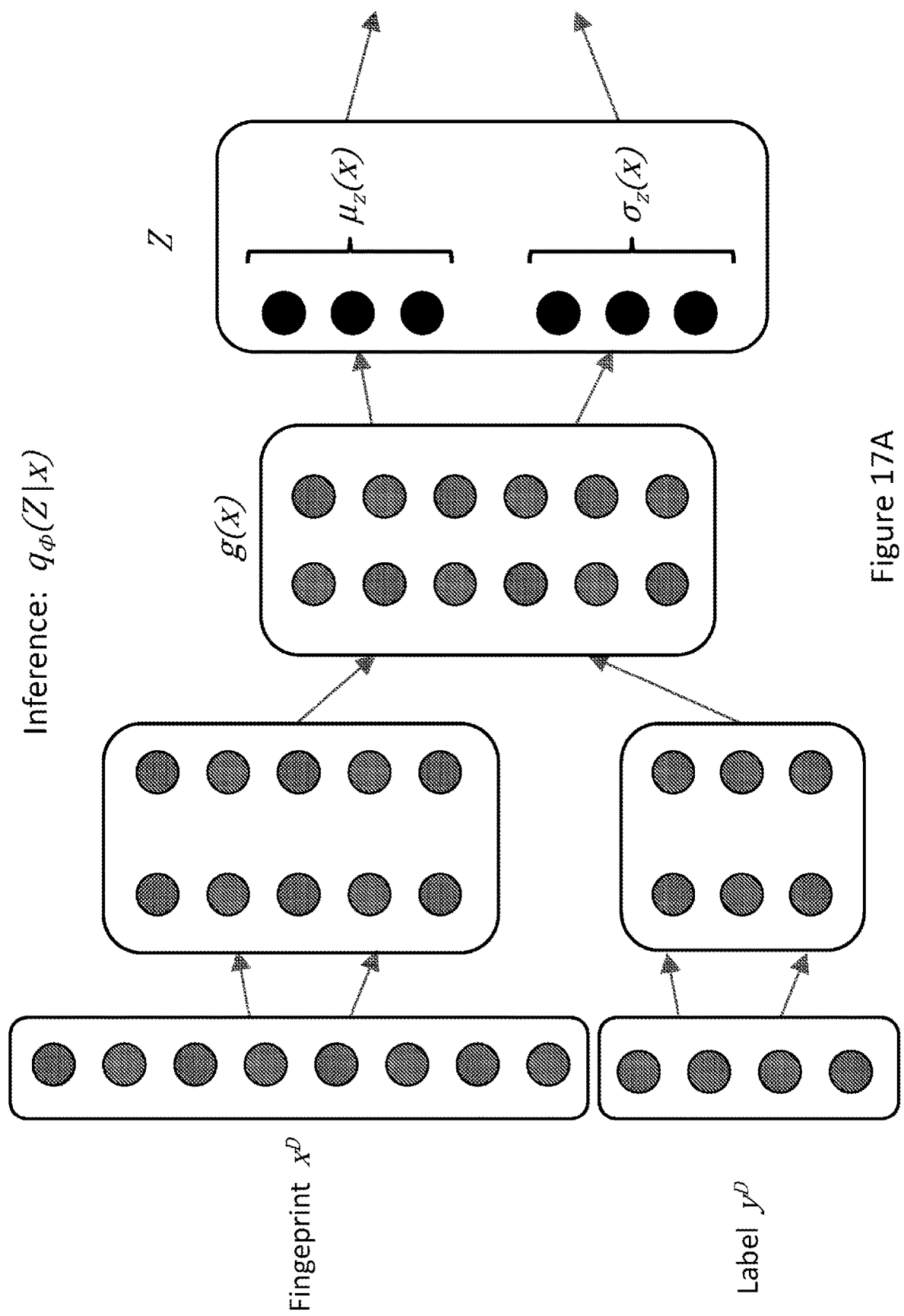
FIG. 17A depicts an exemplary illustration of alternative configurations of input layers for fingerprints and labels in machine learning models, wherein fingerprints and labels are input into the same layer of a machine learning model.
Figure 17B:
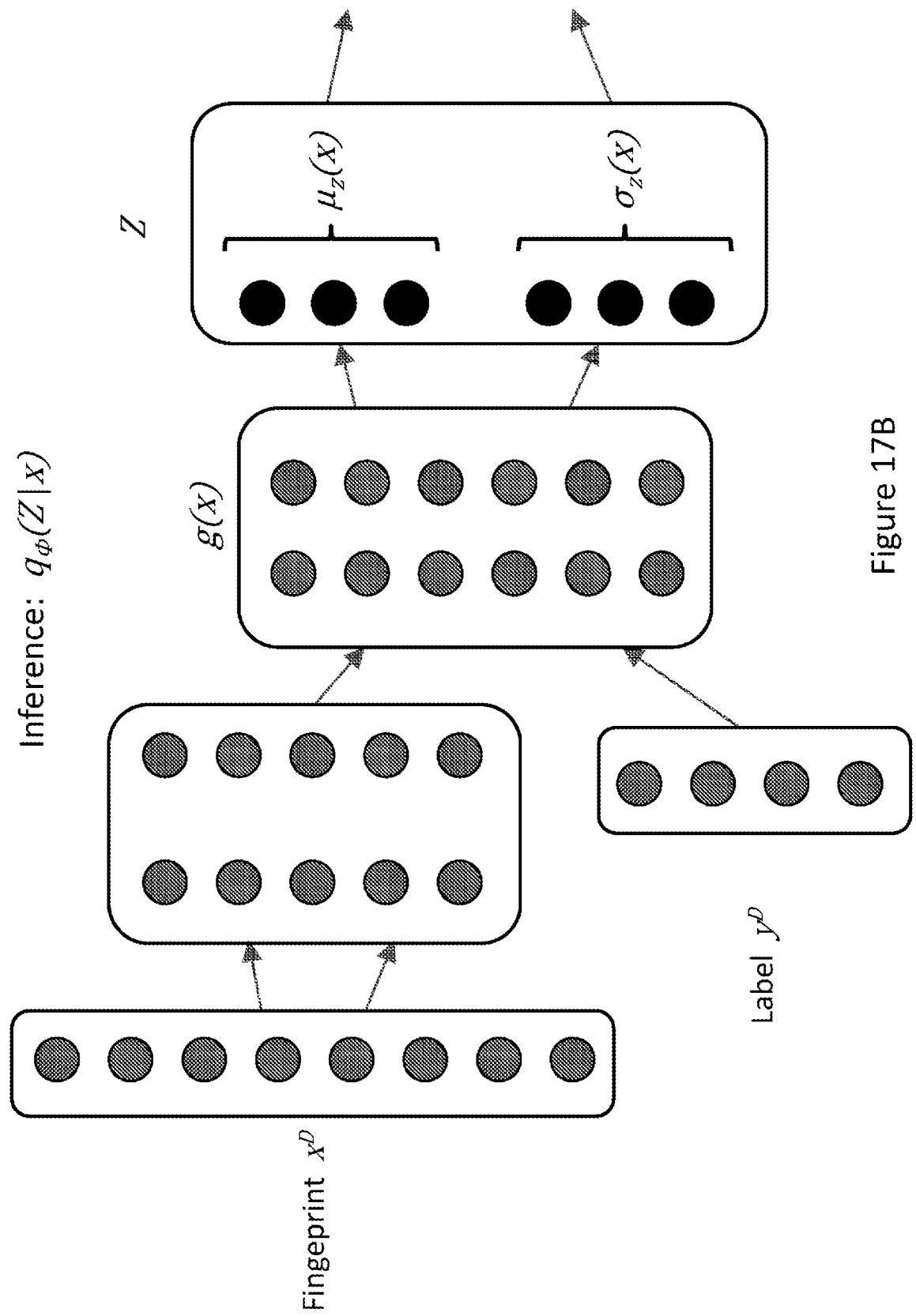
FIG. 17B depicts an exemplary illustration of alternative configurations of input layers for fingerprints and labels in machine learning models wherein fingerprints and labels are input into different layers of a machine learning model.

FIGS. 2A and 2B exemplify the use of a generative model in which label information is provided to the model at two or more levels. Further, machine learning models, according to various embodiments of the invention, may be configured to accept chemical compound representations and labels at the same (FIG. 17A) or different layer(s) (FIG. 17B) of the machine learning model. For example, chemical compound representations may be passed through one or more layers of an encoder and labels associated with each chemical compound representation may be input at a later layer of the encoder.

The systems and methods of the invention described herein can utilize representations of chemical compounds, such as fingerprinting data. Label information associated with a part of the data set may be missing. For example, for some compounds assay data may be available, which can be used directly in the training of the generative model. In other cases, label information may be not available for one or more compounds. In certain embodiments, the systems and methods of the invention comprise a predictor module for partially or completely assigning label data to a compound and associating it with its fingerprint data. In an exemplary embodiment of semi-supervised learning, the training data set used for training the generative model contains both compounds that have experimentally identified label information and compounds that have labels predicted by the predictor module. (FIG. 2B).

The predictor may comprise a machine learning classification model. In some embodiments, the predictor is a deep neural network with two, three, four, five, six, seven, eight, nine, ten, eleven, twelve, thirteen, fourteen, fifteen, sixteen, or more layers. In some embodiments, the predictor is a random forest classifier. In some embodiments, the predictor is trained with a training data set comprising chemical compound representations and their associated labels. In some embodiments, the predictor may have been trained previously, on a set of chemical compound representations and their associated labels that is different from the training data set used to train the generative model.

Fingerprints that were initially unlabeled for one or more label elements may be associated with a label element value for one or more label elements by the predictor. In one embodiment, a subset of the training data set may comprise fingerprints that do not have associated labels. For example, compounds that may be difficult to prepare and/or difficult to test may be completely or partially unlabeled. In this case, a variety of semi-supervised learning methods may be used. In one embodiment, the set of labeled fingerprints is used to train the predictor module. In one embodiment, the predictor implements a classification algorithm, which is trained with supervised learning. After the predictor has been trained sufficiently, unlabeled fingerprints may be input to the predictor in order to generate a predicted label. The fingerprint and its predicted label are then added to the training data set, which may be used to train the generative model.

Predictor-labeled chemical compounds may be used to train the first generative model or a second generative model. The predictor may be used to assign label element values y to a fingerprint feature vector $x^D$ that lacks label information. By the use of the predictor, the generative model herein may be trained on a training data set partially comprising predicted labels. Generative models described in further detail elsewhere herein, once trained, may be used to create generated representations of chemical compounds, such as fingerprints. Generated representations of chemical compounds may be produced based on a variety of conditions imposed by desired labels.

In some embodiments, the generative model is used to generate representations of new chemical compounds that were not presented to the model during the training phase. In some embodiments, the generative model is used to generate chemical compound representations that were not included in the training data set. In this way, novel chemical compounds that may not be contained in a chemical compound database, or may not have even been previously conceived, may be generated. The model having been trained on a training set comprising real chemical compounds may have certain advantageous characteristics. Without being bound by theory, training with real chemical compound examples or with drugs, which have a higher probability to work as functional chemicals, may teach the model to generate compounds or compound representations that may possess similar characteristics with a higher probability than, for example, hand-drawn or computationally generated compounds using residue variation.

The compounds associated with the generated representations may be added to a chemical compound database, used in computational screening methods, and/or synthesized and tested in assays.

In some embodiments, the generative model is used to generate compounds that are intended to be similar to a specified seed compound. Compounds similar to a seed may be generated by inputting a seed compound and its associated label to the encoder. A latent representation of the seed compound and the desired label are then input to the decoder. Using the representation of the seed compound as the starting point, the decoder generates a random variable from which a sample may be drawn. The sample may comprise a fingerprint of a compound that is expected to have some similarity to the seed compound and/or to have a high likelihood of meeting the requirements defined by the desired label.

In some embodiments, the generative model is used to generate chemical compound representations by specifying a desired label, i.e., a set of desired label element values. Based on the modeled joint probability distribution, the generative model may generate one or more compound representations for which the represented compounds have a high likelihood of satisfying the requirements of the specified label element values. In various embodiments, the methods and systems described herein may be used for training a generative model, generating representations of chemical compounds, or both. A generation phase may follow the training phase. In some embodiments, a first party performs the training phase and a second party performs the generation phase. The party performing the training phase may enable replication of the trained generative model by providing parameters of the system that are determined by the training to a separate computer system under the possession of the first party or to a second party and/or to a computer system under the possession of the second party. Therefore, a trained computer system, as described herein, may refer to a second computer system configured by providing to it parameters obtained by training a first computer system using the training methods described herein, such that the second computer system is capable of reproducing the output distribution of the first system. Such parameters may be transferred to the second computer system in tangible or intangible form.

The training phase may comprise using labeled fingerprint data to train the generative model and the predictor concurrently.

In the generation phase, a part of the computer systems described herein, for example a probabilistic decoder, may be used to produce generated representations of chemical compounds, e.g. fingerprints. The systems and methods described herein may generate these representations in a way to maximize the probability of the desired outcomes for selected labels, for example bioassay results, associated with the generated representations. In some embodiments, generated representations are created ab initio, i.e., by drawing a latent representation from a known distribution, such as a standard normal distribution. In some embodiments, a comparative approach is used in the generation phase. For example, a seed compound and its associated label may be input to the encoder, which outputs a latent variable from which a latent representation may be sampled. In turn, the latent representation and the desired label may be jointly input to the decoder. Training algorithms described herein may be adapted to the particular configuration of the generative model that is employed within the computer systems and methods described in further detail elsewhere herein. It is to be understood that methods known in the art, such as cross-validation, dropout, or denoising, may be used as part of the training process.

In some embodiments, the predictor may use a classifier such as random forest, gradient boosted decision tree ensemble, or logistic regression.

A variety of suitable training algorithms can be selected for the training of the generative models of the invention described elsewhere herein in further detail. The appropriate algorithm may depend on the architecture of the generative model and/or on the task that the generative model is desired perform. For example, a variational autoencoder may be trained to optimize the variational lower bound with the combination of variational inference and stochastic gradient ascent.

A regularization constraint may be imposed by a variety of ways. In some embodiments, methods known in the art such as dropout, denoising, or sparse autoencoders may be used.

Generation Procedure

In various embodiments, the methods and systems described herein are used to generate representations of chemical compounds. These generated representations may not have been part of the training data set that was used to train the model. In some embodiments, chemical compounds associated with the generated representations may be novel to the generative model that produced it.

The generated representations and/or related chemical compounds may be produced from a generative model that was never presented with the generated representation and/or related chemical compound. In some embodiments, the generative model was not presented with the generated representation and/or related chemical compound during the training phase.

In some cases, the methods and systems described herein may be used to output generated representations of chemical compounds upon creating a trained generative model with a training data set. Thus, the information in the training data set, such as chemical structures of the chemical compounds and their characteristics may inform the generation phase and the generated representations of chemical compounds.

In various embodiments, generative models described herein generate representations of compounds that have a high likelihood of displaying the activities and possessing the properties specified in a desired label. For example, the desired label may contain specified activities on specific bioassay tests, such as activity with certain receptors or enzymes. Compounds can be characterized by a number of molecular descriptors, such as formula, structures, density of electricity, or other chemical characteristics or any other suitable molecular descriptors known in the art. Physical properties as well as descriptors related to the line drawing of a chemical compound may be used. Electric field of the ligand, for example arising from a Comparative Molecular Field Analysis (CoMFA) may also be used. Molecular descriptors, may include, but are not limited to molar refractivity, octinol/water partition coefficients, $pK_a$, number of atoms for specific elements, such as carbon, oxygen, or halogen atoms, atom pair descriptors, numbers of specific types of bonds, such as rotatable bonds, aromatic bonds, double bonds or triple bonds, hydrophilicity and/or hydrophobicity, number of rings, sums of the positive partial charges on each atom, polar, hydrophobic, hydrophilic, and/or water accessible surface areas, heat of formation, topological connectivity indices, topological shape indices, electro topological state indices, structure fragment counts, surface area, packing density, van der Waals volumes, refractivity, chirality, toxicity, topological indexes, such as the Wiener Index, Randic branching index, and/or Chi index, descriptors based on three dimensional representations, etc. This information may be represented as a fingerprint of each compound. The methods and systems described herein train generative models with labels and chemical compound representations to generate compound representations, such as fingerprints, that are expected to have certain characteristics with respect to a desired label, e.g. a label that specifies desired results on certain bioassays. In some embodiments, the generated representations are later used as lead compounds or initial compounds in a hit-lead procedure.

Generation of Candidates (Ab Initio Case)

Figure 3:
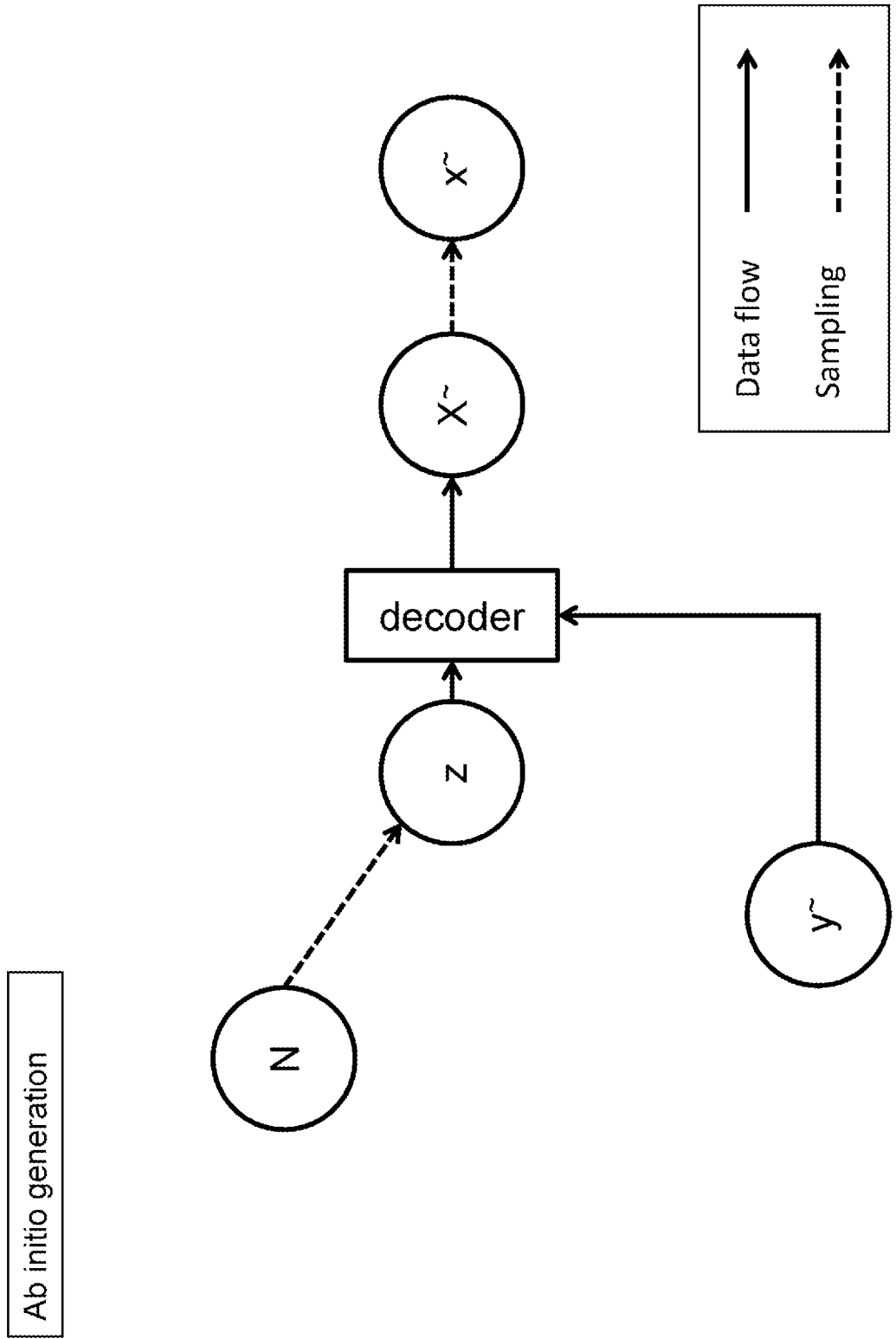
FIG. 3 demonstrates an illustrative example for ab initio creation of generated representations of chemical compounds satisfying requirements set by the desired label $\tilde{y}$.

In the ab initio case, the generation of candidate compounds is constrained only by the desired label y~. Accordingly, ab initio generation may be used when there are no restrictions on the physical structure of the candidate compounds. Because the generated compounds are restricted only by the desired label y~, ab initio generation may be more likely to generate novel compounds that may not yet exist in a chemical compound database. Such results may prove useful in exploratory drug discovery research. In various embodiments, the ab initio generation method is used employing only the sampling module and the decoder. The sampling module may draw a sample from a specified probability distribution that may be different than the probability distribution that was used to train the generative model. FIG. 3 demonstrates an illustrative example of ab initio creation in which the sampling module samples from the standard normal distribution. This generates a latent representation z that may have no similarity to a known chemical compound. The latent representation z and the desired label y~ may both be input to the decoder. From these inputs, the decoder may generate a random variable X~ over a distribution of molecular descriptors (e.g. fingerprints) likely to meet the requirements of desired label y~.

The sampling module then samples from this random variable to generate x~, which may be the fingerprint for a generated candidate compound.

Generation of Candidates (Comparative Case)

In various embodiments, the systems and methods described herein are utilized to generate representations of chemical compounds, e.g., fingerprints, using a seed compound as a starting point. The seed compound may be a known compound for which certain experimental results are known and it may be expected that the structural properties of the generated compound will bear some similarity to those of the seed compound. For example, a seed compound may be an existing drug that is being repurposed or tested for off-label use and it may be desirable that a generated candidate compound retain some of the beneficial activities of the seed compound, such as low toxicity and high solubility, but exhibit different activities on other assays, such as binding with a different target, as required by the desired label. A seed compound may also be a compound that has been physically tested to possess a subset of desired label outcomes, but for which an improvement in certain other label outcomes, such as decreased toxicity, improved solubility, and/or improved ease of synthesis, is desired. Comparative generation may therefore be used to generate compounds intended to possess structural similarity to the seed compound but to exhibit different label outcomes, such as a desired activity in a particular assay.

In various embodiments, a representation, such as a fingerprint, of a seed compound and its associated label are input to a generative model, such as a trained probabilistic or variational autoencoder. For example, when the fingerprint of the seed compound and its associated label are input to the encoder, the encoder can output a latent variable Z. From the latent variable Z, the sampling module can draw a sample to create a latent representation of the seed compound and its label information. This latent representation and the desired label y~ may be input to the decoder, which can decode them to generate a random variable defined over the space of possible fingerprint values. The sampling module may sample from the random variable to generate a chemical compound representation.

The generative model or individual components thereof may be configured to accept a desired label, y~, as well as latent representations generated based on the seed chemical compound. The original label associated with the seed chemical compound, $y^D$, and the desired label, y~, may differ in various degrees. In some cases, $y^D$ and y~ may differ only with respect to one or more designated aspects, such as with respect to toxicity, while they may not differ with respect to other aspects. For example, $y^D$ and y~ may be the same with respect to a first bioassay and a second bioassay, but may differ with respect to a third bioassay. In some embodiments, the seed compound may not have an associated label that was determined experimentally. In this case, the label $y^D$ of the seed compound may be predicted by the predictor module.

Figure 4A:
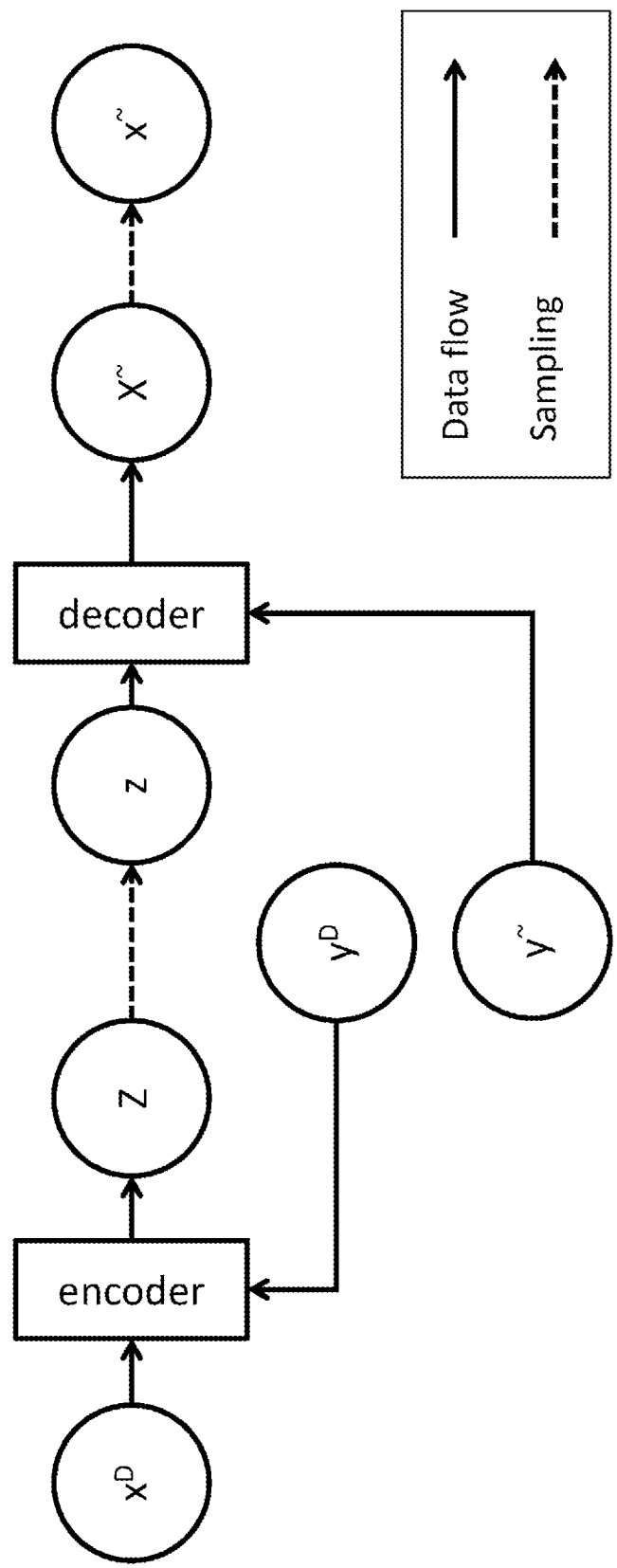
FIG. 4A provides an exemplary illustration for creating generated chemical compound representations based on a labeled seed compound. Compound representation x~ may be generated by using actual label $y^D$ and desired label y~.
Figure 4B:
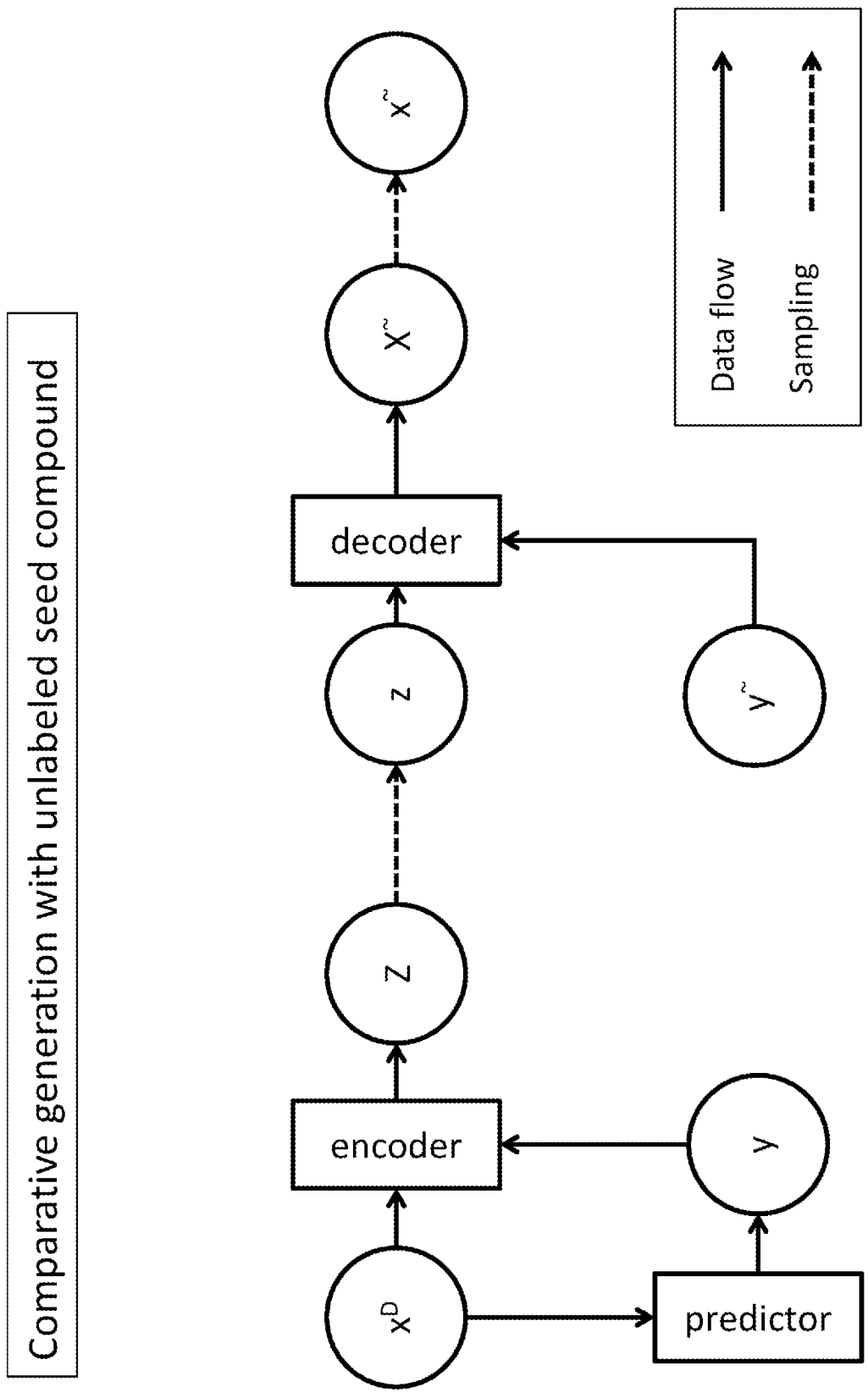
FIG. 4B provides an exemplary illustration for creating an unlabeled seed compound. Compound representation x~ may be generated by using predicted label y, which is generated by a predictor module, and desired label y~.

FIGS. 4A and 4B provide an exemplary illustration for creating generated chemical compound representations based on a seed compound and an associated label. In this embodiment, both the desired label, y~, and a latent representation, z, of the seed compound are input to the decoder. In accordance with the embodiment, the decoder outputs a pair of a vector of means and a vector of standard deviations. These vectors may define a random variable X~ that models the distribution from which a compound that is similar to the seed compound $x^D$ but is associated with the desired label, y~, or in some cases, a close variant of the desired label, y~, is likely to be drawn. A sample may be drawn from random variable X~ to generate a compound representation x~, for example in the form of a fingerprint. In various embodiments, the generative network is trained such that the generated compound x~ is likely to have the set of activities and properties specified in desired label y~.

In some embodiments, chemical compounds corresponding to the generated representations are prepared chemically. The prepared compounds may be tested for having the desired properties or activities as specified in the label used in the generation phase. The prepared compounds may be further tested for additional properties or activities. In some embodiments, the prepared compounds may be tested in clinical use, for example in multi-stage animal and/or human use studies.

Sources of Labels

The training data may be compiled from information of chemical compounds and associated labels from databases, such as PubChem (http://pubchem.ncbi.nlm.nih.gov/). The data may also be obtained from drug screening libraries, combinatorial synthesis libraries, and the like. Label elements that relate to assays may comprise cellular and biochemical assays and in some cases multiple related assays, for example assays for different families of an enzyme. In various embodiments, information about one or more label elements may be obtained from resources such as chemical compound databases, bioassay databases, toxicity databases, clinical records, cross-reactivity records, or any other suitable database known in the art.

Fingerprinting

Chemical compounds may be preprocessed to create representations, for example fingerprints that can be used in the context of the generative models described herein. In some cases, the chemical formula of a compound may be restored from its representation without degeneracy. In other cases, a representation may map onto more than a single chemical formula. In yet other cases, no identifiable chemical formula that can be deduced from the representation may exist. A nearest neighbor search may be conducted in the representation space. Identified neighbors may lead to chemical formulas that may approximate the representation generated by the generative model.

In various embodiments, the methods and systems described herein utilize fingerprints to represent chemical compounds in inputs and/or outputs of generative models.

Molecular descriptors of various types may be used in combination to represent a chemical compound as a fingerprint. In some embodiments, chemical compound representations comprising molecular descriptors are used as input to various machine learning models. In some embodiments, the representations of the chemical compounds comprise at least or at least about 50, 100, 150, 250, 500, 1,000, 2,000, 3,000, 4,000, 5,000, or more molecular descriptors. In some embodiments, the representations of the chemical compounds comprise fewer than 10,000, 7,500, 5,000, 4,000, 3,000, 2,000, 1,000, 500, 250, 150, 200, or 50 molecular descriptors.

The molecular descriptors may be normalized over all the compounds in the union of all the assays and/or threshold.

Chemical compound fingerprints typically refer to a string of values of molecular descriptors that contain the information of a compound's chemical structure (e.g. in the form of a connection table). Fingerprints can thus be a shorthand representation that identifies the presence or absence of some structural feature or physical property in the original chemistry of a compound.

In various embodiments, fingerprinting comprises hash-based or dictionary-based fingerprints. Dictionary-based fingerprints rely on a dictionary. A dictionary typically refers to a set of structural fragments that are used to determine whether each bit in the fingerprint string is 'on' or 'off'. Each bit of the fingerprint may represent one or more fragments that must be present in the main structure for that bit to be set in the fingerprint.

Some fingerprinting applications may use the "hash-coding" approach. Accordingly, the fragments present in a molecule may be "hash-coded" to fingerprint bit positions. Hash-based fingerprinting may allow all of the fragments present in the molecule to be encoded in the fingerprint. However, hash-based fingerprinting may cause several different fragments to set the same bit, thus leading to ambiguity.

Generating representations of chemical compounds as fingerprints may be achieved by using publicly available software suites from a variety of vendors. (See e.g. www.talete.mi.it/products/dragon_molecular-descriptor_1-istpdf, www.talete.mi.it/products/dproperties_molecular_descriptors.htm, www.moleculardescriptors.eu/softwares/softwares.htm, www.dalkescientific.com/writings/diary/archive/2008/06/26/fingerprint_background.html, or vega.marionegri.it/wordpress/resources/chemical-descriptors).

Methods

An important benefit of this invention is the ability to discover drugs that may have fewer side effects. The generative models described herein may be trained by including in the training data set compound activities for particular assays for which certain results are known to be responsible for causing side effects and/or toxic reactions in humans or animals. Accordingly, a generative model may be taught the relationships between chemical compound representations and beneficial and unwanted effects. In the generation phase, a desired label y~ input to the decoder may specify desired compound activity on assays associated with beneficial effects and/or unwanted side effects. The generative model can then generate representations of chemical compounds that simultaneously satisfy both beneficial effect and toxicity/side effect requirements.

By simultaneously satisfying desired outcomes for beneficial effects and unwanted side effects, the methods and systems described herein enable more efficient exploration in the earlier stages of the drug discovery process, thereby possibly reducing the number of clinical trials that fail due to unacceptable side effects of the tested drug. This may lead to reductions in both the duration and the cost of the drug discovery process.

In some embodiments, the methods and systems described herein are used to find new targets for chemical compounds that already exist. For example, the generative networks described herein may produce a generated representation for a chemical compound based on a desired label, wherein the chemical compound is known to have another effect. Accordingly, a generative model trained with multiple label elements, may generate a representation for a chemical compound that is known to have a first effect, in response to the use of the generative phase by inputting a desired label for a different effect, effectively identifying a second effect. Thus, the generative model may be used to identify a second label for a pre-existing chemical compound. Chemical compounds so determined are particularly valuable, as repurposing a clinically tested compound may have lower risk during clinical studies and further, may be proven for efficacy and safety efficiently and inexpensively.

In some embodiments, the generative models herein may be trained to learn the value for a label element type in a non-binary manner. The generative models herein may be trained to recognize higher or lower levels of a chemical compound's effect with respect to a particular label element. Accordingly, the generative models may be trained to learn the level of effectiveness and/or the level of toxicity or side effects for a given chemical compound.

While the methods and systems described herein are particularly powerful in generating representations of chemical compounds, including chemical compounds that were not presented to the model and/or chemical compounds that did not previously exist, thereby enlarging chemical compound libraries. Further, the various embodiments of the invention also facilitate conventional drug screening processes by allowing the output of the generative models to be used as an input dataset for a virtual or experimental screening process.

In various embodiments, the generated representations relate to chemical compounds having similarity to the chemical compounds in the training data set. The similarity may comprise various aspects. For example, a generated chemical compound may have a high degree of similarity to a chemical compound in the training data set, but it may have a much higher likelihood of being chemically synthesizable and/or chemically stable than the chemical compound in the training data set to which it is similar. Further, a generated compound may be similar to a chemical compound in the training data set, but it may have a much higher likelihood of possessing desired effects and/or lacking undesired effects than existing compound in the training data set.

In various embodiments, the methods and systems described herein generate chemical compounds or representations thereof taking into account their ease of synthesis, solubility, and other practical considerations. In some embodiments, generative models are trained using label elements that may include solubility or synthesis mechanisms. In some embodiments, a generative model is trained using training data that includes synthesis information or solubility level. Desired labels related to these factors may be used in the generation phase to increase the likelihood that the generated chemical compound representations relate to compounds that behave according to the desired solubility or synthesis requirements. In various drug discovery applications, multiple candidate fingerprints may be generated. A set of generated fingerprints can then be used to synthesize actual compounds that can be used in high throughput screening. Prior to compound synthesis and HTS, it is useful to evaluate whether the generated fingerprints have the desired assay results and/or structural properties. Generated fingerprints may be evaluated based on their predicted results and their similarity to the seed compound (in comparative generation). If the generated fingerprints have the desired properties, they may be ranked based on their druglikeness.

Additional system modules can be introduced for these procedures: A comparison module may be used to compare two fingerprints or two sets of assay results. A ranking module may be used to rank the members of a set of fingerprints by a druglikeness score. A classifier may be used to classify a compound fingerprint by assigning a druglikeness score. And an ordering module may be used to order a set of scored fingerprints.

In various embodiments, the methods and systems of the invention may be used to evaluate predicted results of generated compounds and/or to rank the generated compounds. In various embodiments, the predicted assay results of generated fingerprints are compared to the desired assay results. Fingerprints having predicted results that match the desired assay results may be ranked for additional considerations, for example by a druglikeness score.

Figure 7:
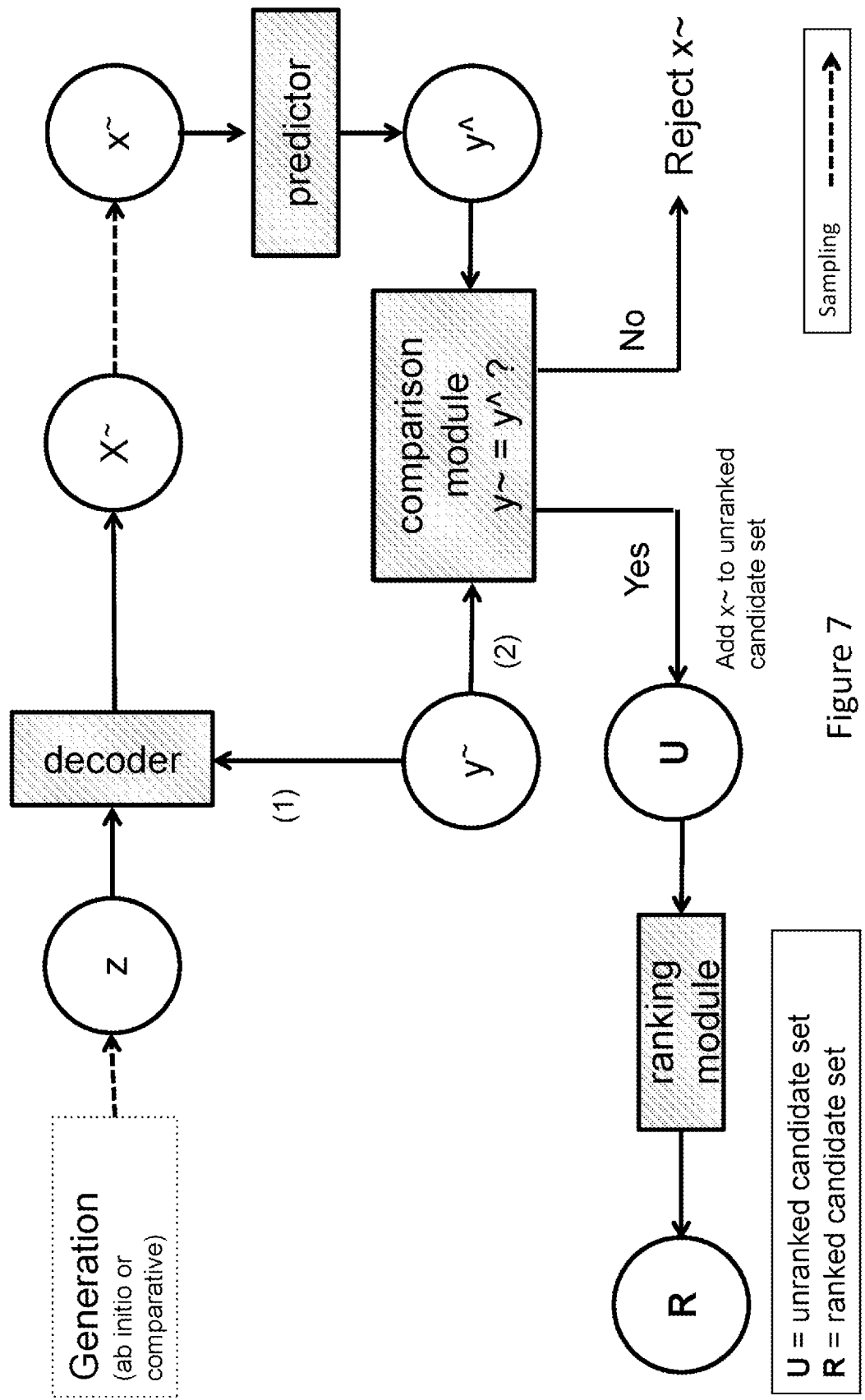
FIG. 7 depicts an illustrative example of a single step evaluation and ranking procedure according various embodiments of the invention.

FIG. 7 depicts an illustrative example of a single step evaluation and ranking procedure according to various embodiments of the invention. Generated representations x~ may be produced according to various methods described herein, for example by ab initio or comparative generation. Generated representations x~, for example representations in the form of a fingerprint, or related chemical compounds, may be input to a trained predictor module. (The predictor module may, for example, have been trained during a semi-supervised learning process for unlabeled data.) The predictor module can output ŷ, the predicted set of assay results for the generated representation x~.

The predicted assay results ŷ and the desired assay results y~ may be input to a comparison module (FIG. 7). The comparison module may be configured to compare the predicted results and the desired results. If the comparison module determines that the predicted results are the same as the desired results, x~ may be added to a set of unranked candidates, U; otherwise, x~ may be rejected. The unranked set may be ranked by a ranking module as described in further detail elsewhere herein.

In various embodiments, the methods and systems of the invention may be used to evaluate generated representations, for example fingerprints generated through comparative generation.

Figure 8:
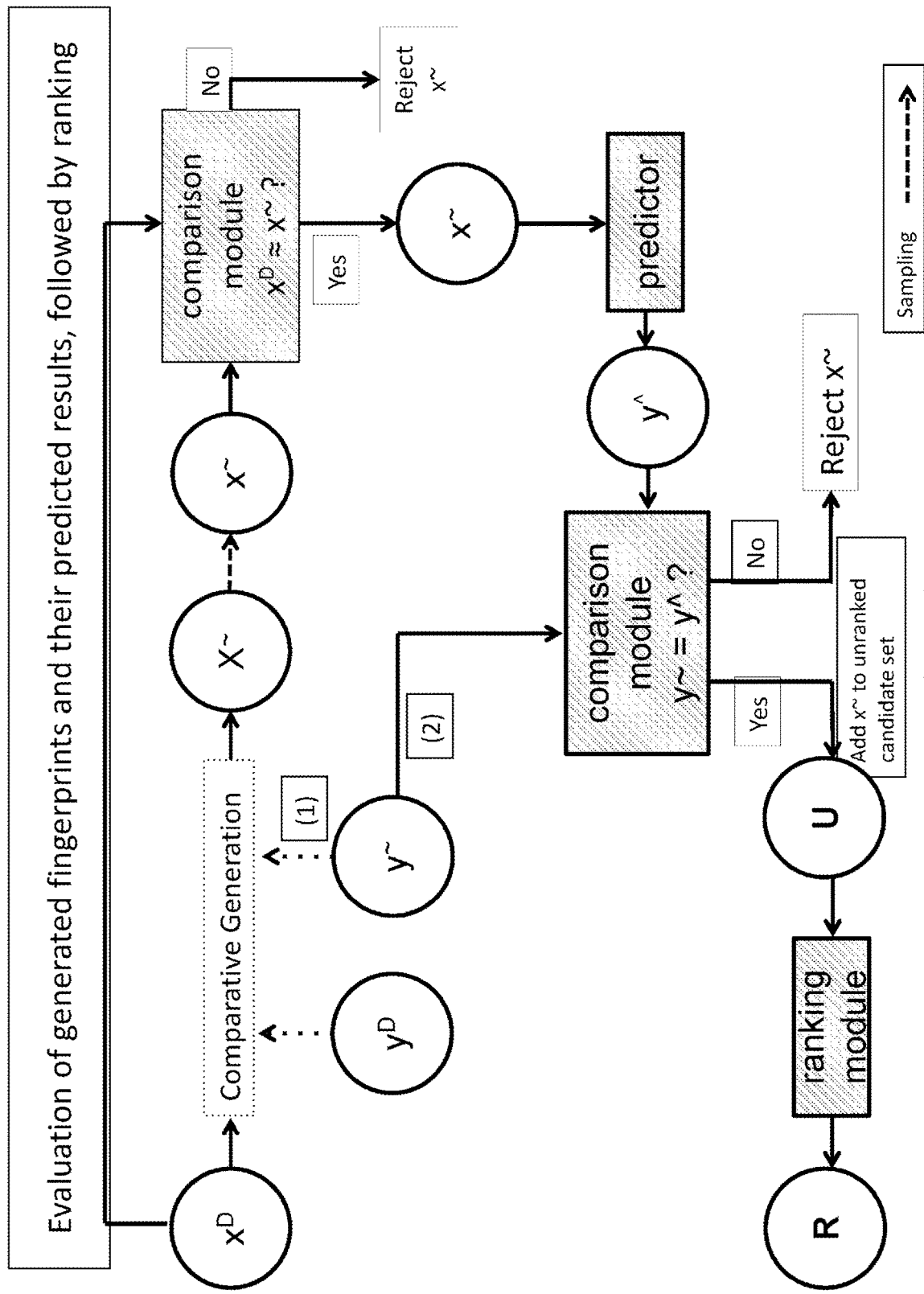
FIG. 8 depicts an illustrative example of an evaluation method of generated fingerprints and their predicted results, according to various embodiments of the invention.

In comparative generation, a seed compound may be used in order to generate a novel fingerprint that is similar to the seed. Following comparative generation processes, an evaluation step may be used to determine whether the generated fingerprint is sufficiently similar to the seed. In this embodiment, a comparison module may be used to compare corresponding parameters of two fingerprints, typically a generated representation and a seed compound's fingerprint. If a threshold of identical parameters or a threshold similarity is reached, the two fingerprints may be marked as sufficiently similar FIG. 8 depicts an illustrative example of an evaluation method of generated fingerprints and their predicted results, according to various embodiments of the invention. Accordingly, a generated representation x~, and the associated seed compound representation $x^D$ are input to a comparison module. The comparison module may be configured to first compare x~ and $x^D$ for similarity. If the comparison module determines that x~ is sufficiently similar to $x^D$, x~ may be retained. If not, x~ may be rejected.

In various embodiments, retained generated representations x~ may be input to a predictor module as described in further detail elsewhere herein. The predictor module may be used to output a predicted label ŷ. A comparison module may be used to compare the predicted label ŷ to the desired label y~. (The desired label y~ may have been used to produce the generated representations during comparative generation with seed compound representation $x^D$.) For a generated representation x~, if the comparison module finds sufficient similarity between ŷ and y~, x~ may be added to an unranked candidate set, U. The unranked set U may be ranked by a ranking module. The ranking module may output a ranked set, R, comprising generated representations.

The systems and methods described herein, in various embodiments of the invention, utilize a ranking module. A ranking module may be configured to have several functions, including assigning a druglikeness score to each fingerprint, and ranking a set of fingerprints according to their druglikeness scores.

A common existing method of assessing a compound's druglikeness is to check the compound's compliance with Lipinski's Rule of Five. Additional factors, such as the logarithm of partition coefficient (log P) and molar refractivity, may also be used. However, simple filtering methods, such as whether a compound's log P and molecular weight are in a certain range, may allow only for a classification analysis, assigning a pass or fail value. Further, in some cases, the standard druglikeness properties may not provide sufficient discriminatory power to evaluate compounds accurately. (For example, the highly successful drugs Lipitor and Singulair both fail two or more of Lipinski's rules; they would have been rejected by a simple filtering process.)

In some embodiments, a desirable ranking of compounds may be achieved by ranking modules described herein. Rather than relying on filtering standard druglikeness properties, a ranking module, according to various embodiments of the invention, evaluates chemical compound representations, such as fingerprints, based on their latent representations. Without being bound by theory, a latent representation of a compound's fingerprint represents high-level abstractions and non-linear combinations of features that may provide a more accurate explanation of the behavior of the compound than standard druglikeness properties are able to provide.

Figure 9:
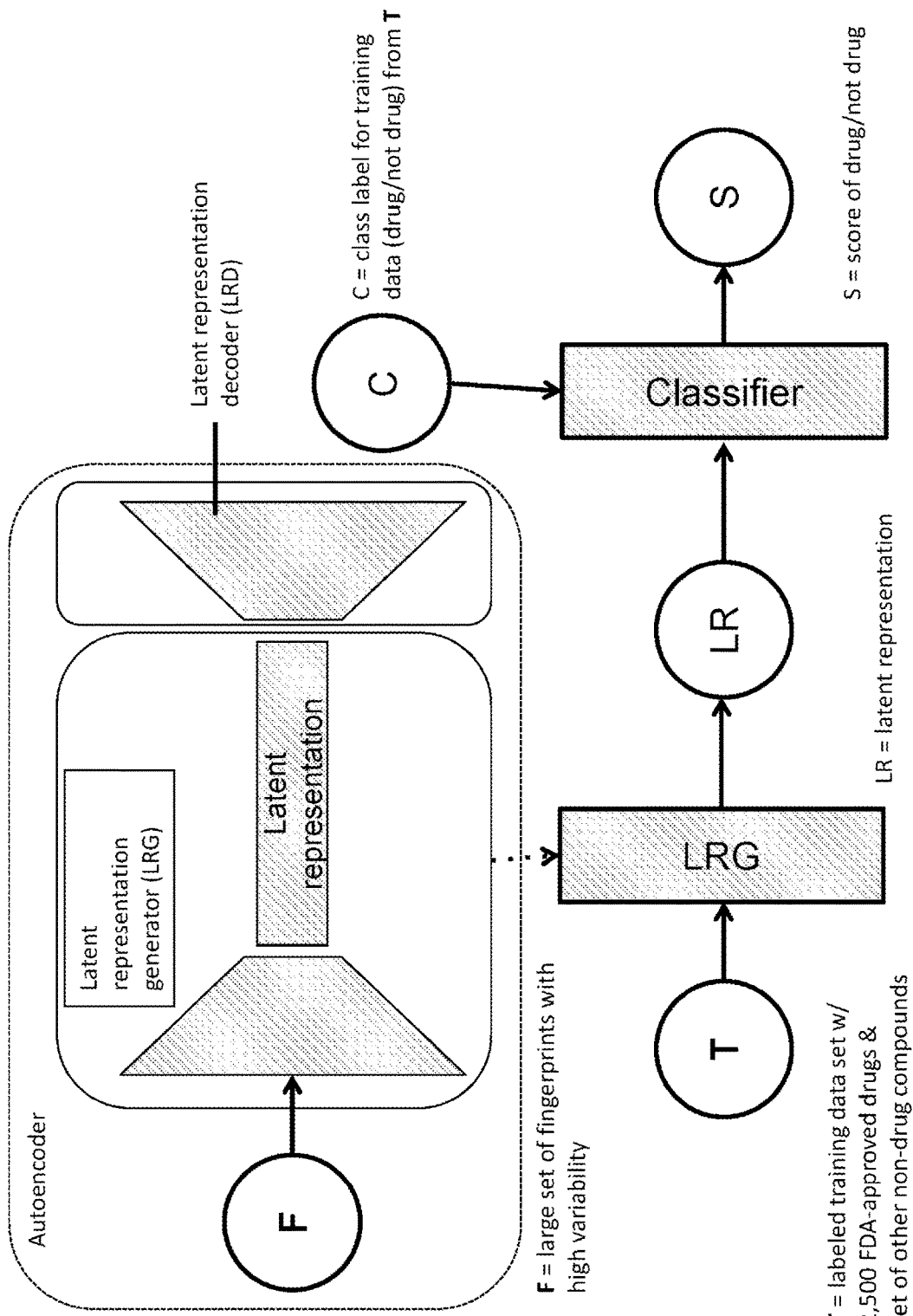
FIG. 9 depicts an exemplary illustration of a training method for a ranking module.

FIG. 9 depicts an exemplary illustration of a training method for a ranking module. In various embodiments, an autoencoder is trained on a large set of chemical compound representations. A latent representation generator (LRG) may form the first part of the autoencoder, in a similar position as an encoder. The LRG can be used to generate latent representations of compounds (LRs). The latent representations may be input to a classifier. The classifier may be trained with supervised learning. The training data set of the classifier may comprise labeled drug and non-drug compounds. The classifier may be trained to output a continuous score that represents the compound's druglikeness.

Figure 10:
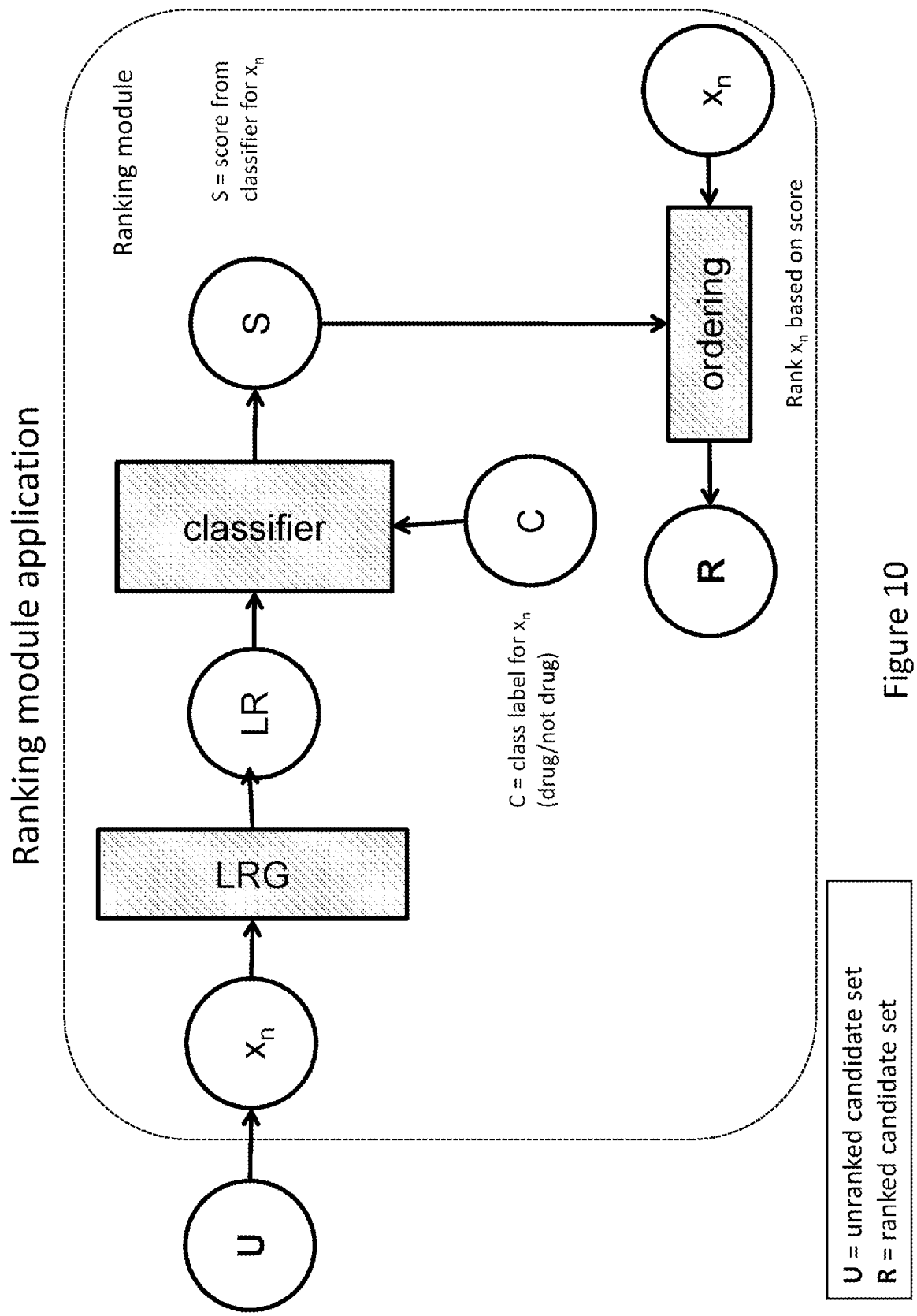
FIG. 10 depicts an exemplary illustration of a ranking module comprising latent representation generator (LRG), classifier, and ordering modules according to various embodiments of the invention.

FIG. 10 depicts an exemplary illustration of a ranking module comprising LRG, classifier, and ordering modules according to various embodiments of the invention. Members of the unranked set of compound representations may be input to the latent representation generator (LRG) and the latent representations may be input into the classifier. The classifier may be configured to provide a druglikeness score for each latent representation. The compound representations and/or the associated compounds, may be ordered, for example from highest druglikeness score to lowest druglikeness score. The ranking module may be used to provide as an output a ranked set of compound representations, e.g. fingerprints, and/or compounds.

In various embodiments of the invention, the systems and methods described herein relate to exploration of a novel compound space through ab initio and comparative generation. According to various embodiments, ab initio and comparative generation may be utilized in sequence. The systems and methods described herein may be used to generate a novel compound, or a representation, e.g. a fingerprint, therefore, that satisfies a certain set of assay results Similar compounds in the representation space surrounding a compound representation may be explored using the systems and methods described herein. For example, an initial compound representation may be generated using an ab initio or comparative generation process with a desired label and one or more generated representations may be output. The compound space around the generated representations may then be explored around these initial representations. According to various embodiments, ab initio and comparative generation may be used in sequence.

Figure 11:
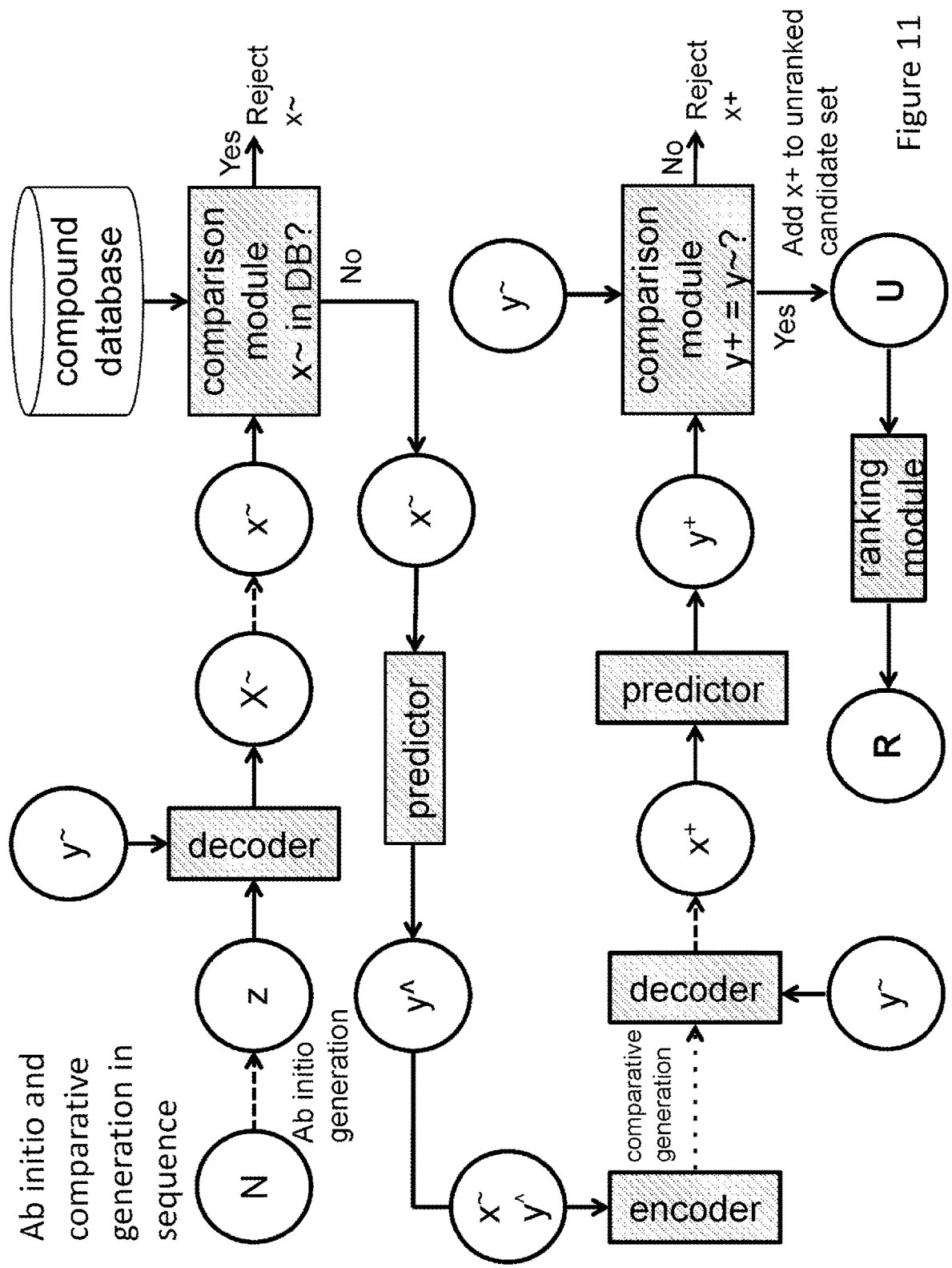
FIG. 11 depicts an exemplary illustration of the sequential use of ab initio and comparative generation processes.
Figure 12:
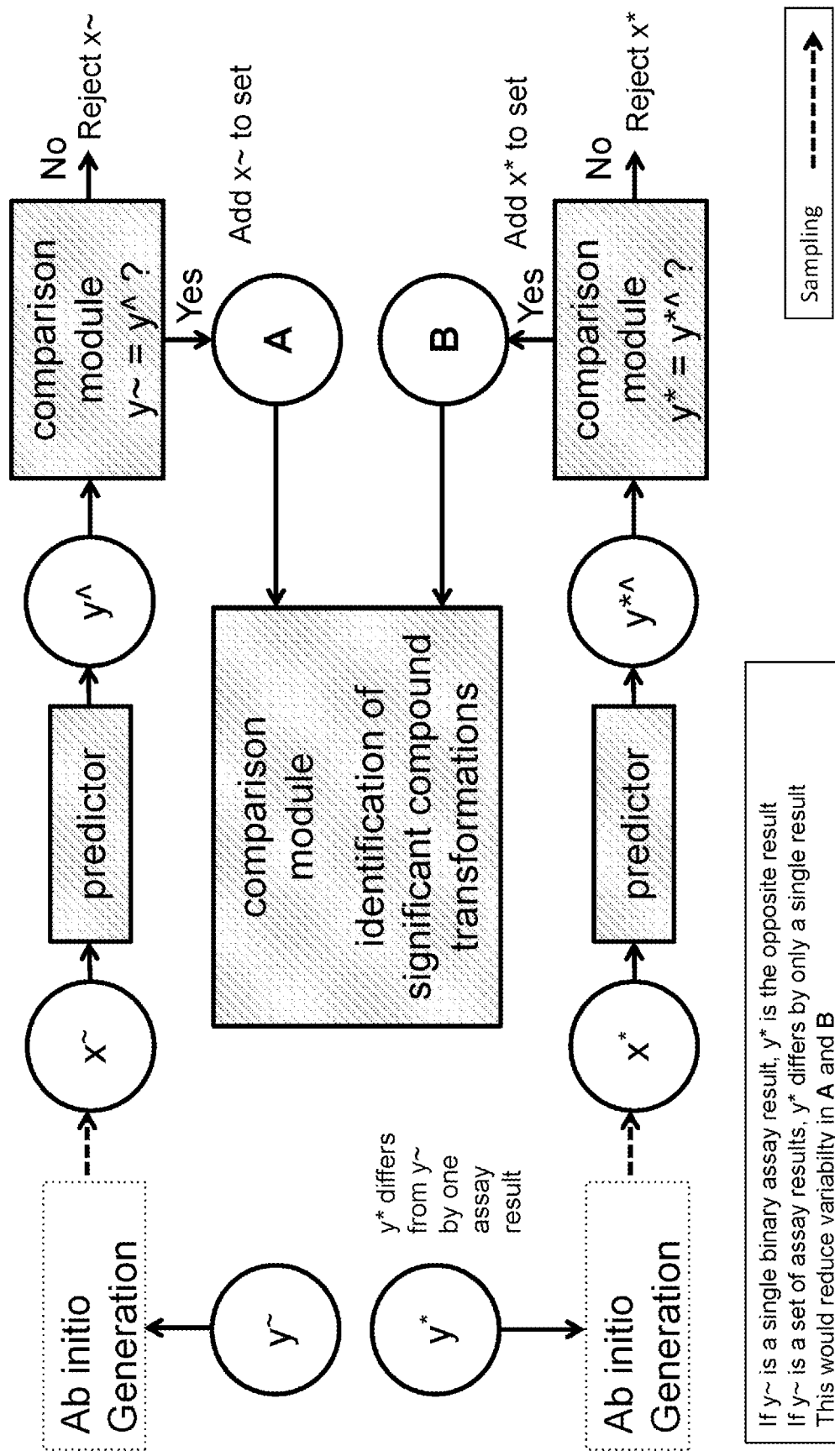
FIG. 12 depicts an exemplary method and system for identification of compound properties that may affect a change in a label or label element value.

FIG. 11 depicts an exemplary illustration of the use of ab initio and comparative generation in sequence. Such a combination may be used to explore the compound space around an initial compound associated with a desired label. Accordingly, based on a desired assay result y~, fingerprint x~ may be generated using ab initio generation. Previously unknown compounds may be prioritized by applying a filter with the use of a comparison module. The comparison module can compare x~ to a database of known compounds. If the comparison module determines that x~ already exists in a database of known compounds, x~ may be flagged for rejection. If the comparison module determines that x~ is a previously unknown compound, x~ may be input to a predictor. The predictor may generate predicted assay results y^ for x~.

By using representation x~ and its predicted assay results y^ as the seeds for comparative generation, a new representation x+ may be generated. A predictor may be used to generate predicted assay results y+ of x+. A comparison module may be used to determine whether y+ is the same as or similar to the desired assay results y~. Upon a finding of identity or sufficient similarity, x+ may be marked for retention. Retained representations may be added to a set U of unranked candidates. Any desired number of fingerprints x+ may be generated from the initial seed of x~ and y^ by repeated application of comparative generation.

The unranked set of candidate representations U may be input to a ranking module. The ranking module may output a ranked set R of compound representations and/or associated compounds.

In various embodiments, the systems and methods described herein may be used to identify compound properties that may affect results on a specific assay. Without being bound by theory, a small number of specific structural properties may be the transformations that change the compound's performance on a particular assay. In various embodiments, the systems and methods described herein provide processes to identify candidate transformations that are associated with a compound's performance on a particular assay. Identified candidate transformations may be used as a starting point for Matched Molecular Pair Analysis (MMPA).

In an exemplary embodiment, two generation processes, for example two ab initio generation processes, are run employing different seed labels. In one, a desired label, y~, is used as a positive seed. In the other, an opposite label, y*, is used as a negative seed. For example, if y~ is a single binary assay result, the negative seed y* may be the opposite result for that assay. Without being bound by theory, using a single assay result may lead to undesirably large variability in the resulting generated fingerprints. To reduce variability, a vector of label elements may be used as the positive seed, y~. For example, if y~ consists of a vector of label element values, y* may differ from y~ by only a single label element value, for example on an assay result of interest.

Accordingly, in various embodiments, two sets of compound representations, A and B, may be generated from the two generation processes. The set A may contain compounds generated from the positive seed, y~. The set B may contain compounds generated from the negative seed, y*. The two sets of compound representations may be input to a comparison module. The comparison module may be configured to identify the compound representation parameters that are most likely to be responsible for the difference in label or label element of interest. Comparison modules described in further detail elsewhere herein.

In some embodiments, more than two ab initio generation processes, each using a different label, may be used to generate a plurality of sets of compounds in a manner similar to that described above for the embodiment with two generation processes. The sets may be analyzed to identify important transformations in the compound representations that may be associated with different label values.

Figure 13:
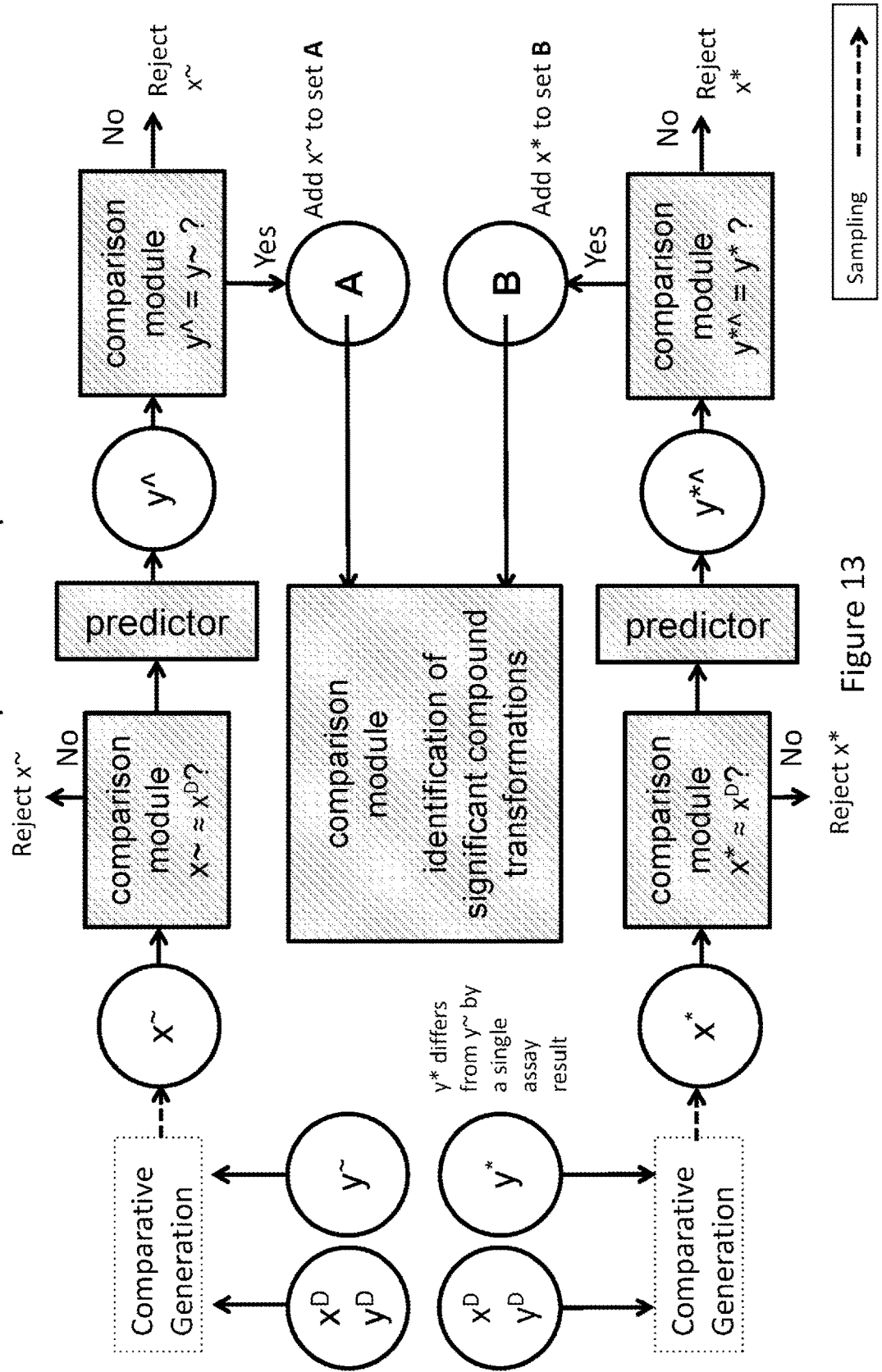
FIG. 13 depicts system and method for the identification of transformations in a specific compound that may be related to a desired label or label element value.

In various embodiments, the systems and methods described herein may be used to explore transformations related to a desired label element value for a specific compound, i.e. transformations in a specific compound that may be responsible for a specific label element value. In some embodiments, the method is performed by running two comparative generation processes with the same seed compound representation, but with different target labels or label element values. The two comparative generation processes may be run in parallel and two sets of compound representations may be generated. A comparison module may be used to identify specific structural differences between representations generated with the positive result and those generated with the negative result (FIG. 13).

The generated representations may be evaluated first by their similarity to the seed compound. If they are sufficiently similar, a predictor module may be used to determine predicted label or label element values for each representation. The predicted labels or label element values may be compared to the target labels or label element values (FIG. 13).

The comparative generation process may be run repeatedly. The resulting candidate generated representations may be grouped in two sets, A and B, with the desired cardinality. The members of A may be compared to the members of B by a comparison module. The comparison module may identify consistent and differing structural transformations between the two sets. Comparison modules are explained in further detail in the subsequent examples and elsewhere herein. These structural transformations can be used as starting points for further analysis through MMPA.

In some embodiments, more than two comparative generation processes are used to generate representations using a different label for each process. A plurality of sets of compounds may be generated as described above for the embodiment with two generation processes. The sets may be analyzed to identify important transformations in the compound representations that may be associated with different label values.

In various embodiments, the systems and methods described herein utilize comparison modules. Comparison modules may be configured to have single or multiple functions. For example, a comparison module may consolidate in one module two functions, such as (1) determining whether two vectors of labels, or two compound representations are similar or identical and (2) comparing two sets of compound representations in order to identify those parameters that are most probable to be responsible for a change in the specified label or label element value. In other embodiments, comparison modules may have a single function or more than two functions.

In some embodiments, a comparison module is configured to perform a comparison of two objects for similarity or identity. The comparison may comprise a simple pairwise comparison for similarity or identity, in which the corresponding elements of the two objects, such as two vectors of assay results or two fingerprints, are compared. A threshold, such as a user-specified threshold, may be used to determine whether the two objects pass or fail the comparison. In some embodiments, systems and methods described herein may be used to set the threshold, for example, by determining a threshold that results in a workable grouping of a training set of objects.

In some embodiments, the comparison module is configured to perform comparisons on the latent representations output by a Latent Representation Generator (LRG). The LRG may be used to encode compound representations, such as fingerprints as latent representations. The resulting distributions of latent representations may be compared and a determination of similarity or identity may be made.

In some embodiments, a comparison module is configured to compare sets of objects for identification of significant compound transformations. A number of methods may be used to identify significant compound transformations, for example, when comparing two sets of fingerprints.

In some embodiments, the comparison module uses a linear model to identify significant parameters. Interaction terms could be added to the model, which, without being bound by theory, would address the possibility that interactions between parameters are responsible for a difference in labels or label element values, such as a difference in a particular assay result, toxicity, side effect, or other label elements described in further detail herein or any other suitable label element known in the art.

In some embodiments, the comparison modules are configured to utilize Gini coefficients as a measure of inequality in a population. A Gini coefficient may be calculated for one, some, or all parameters of an object by calculating the mean of the difference between every possible pair of objects, divided by the mean size. Without being bound by theory, a large Gini coefficient for a parameter tends to indicate a high degree of inequality in that parameter between the members of set A and the members of set B. In various embodiments, a desired number of parameters having the largest Gini coefficients may be selected as the parameters most likely to be related to the change in a label or label element value, for example an assay result. The selection may pick the top 1, 2, 3, 4, 5, 6, 7, 8, 9, 10, 11, 12, 13, 14, 15, 16, 17, 18, 19, 20, or more parameters. In some embodiments, the selection picks the parameters having Gini coefficients above a threshold level or parameters with an above threshold likelihood of being associated with a change in label or label element value.

In some embodiments, a classification tree may be used alongside the Gini coefficient calculation. The parameter with the largest Gini coefficient may be selected to be the root of a classification tree. The remainder of the classification tree may be learned, for example by top-down induction. The desired number of significant parameters may be identified by observing the behavior of the tree at the appropriate level.

When the two sets of fingerprints have low cardinality, the Gini coefficient may be directly calculated. Without being bound by theory, as the cardinality of the sets A and B becomes large, direct calculation of the Gini coefficient may become difficult or impractical due to combinatorial explosion. Systems and methods described herein may be configured to utilize methods that reduce the number of required pairwise comparisons between A and B, for example by applying a clustering method. Accordingly, the Gini coefficients of the parameters may be calculated by pairwise comparisons between the centroids of the clusters resulting from the clustering of the members of A and the members of B.

Without being bound by theory, as compound representations have a large number of parameters, e.g. in the thousands or more, directly clustering the members of A and B may become unfeasible because of the dimensionality. A representation of sets A and B in a space with thousands of dimensions may be very sparse. A large number of data points may be needed to achieve statistically significant clustering in the compound representation space. The systems and methods of the invention, in various embodiments, may address these problems by utilizing alternative clustering methods. In some embodiments, the methods and systems of the invention are used to cluster vectors comprising latent representations of the members of A and B. These latent representations may be of lower dimension. Clustering latent representations may be additionally advantageous because a latent representation may capture non-linear combinations of the parameters of the members of A and B. This ability may, in some cases, provide a latent representation with a superior ability to explain the behavior of the compound or specific features thereof, such as a particular chemical residue.

In various embodiments, the systems and methods of the invention are used to cluster compound representations, by performing clustering of related latent representations. For example, the systems and methods of the invention may be used to calculate a Gini coefficient using k-medoids clustering in the latent representation space.

Figure 14:
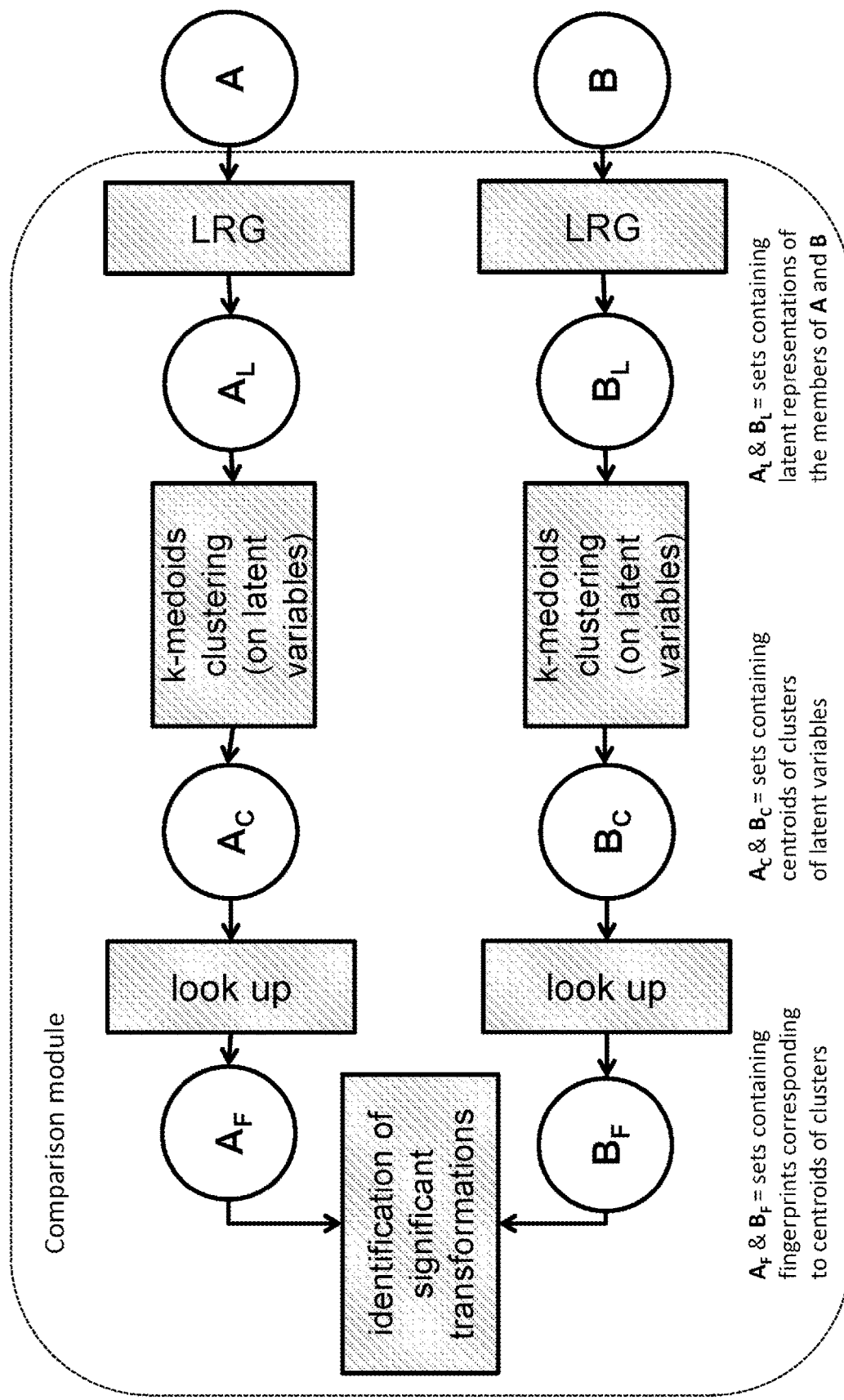
FIG. 14 depicts an exemplary illustration of a comparison module using k-medoids clustering.

FIG. 14 depicts an exemplary illustration of a comparison module using k-medoids clustering. Accordingly, latent representations may be generated for the members of sets A and B. For example, a latent representation generator (LRG) may be used to encode the members of sets A and B as latent representations to form the latent representation sets $A_L$ and $B_L$, respectively. A clustering method, such as k-medoids clustering, may be applied to the members of the latent representation sets. Following clustering, the centroids of the clustered sets may be extracted to form the latent representation centroid sets, $A_c$ and $B_c$. Without being bound by theory, because the centroids in some clustering methods, such as k-medoids clustering, are actual members of the original data set, in the application of such clustering methods, the sets $A_c$ and $B_c$ are expected to contain latent representations of members of the original sets A and B. The compound representations corresponding to the members of $A_c$ and $B_c$ can be looked up to form two sets of fingerprints $A_F$ and $B_F$. The cardinalities of $A_F$ and $B_F$ may be significantly lower than the cardinalities of the original sets A and B. The members of sets $A_F$ and $B_F$ may be used to identify compound transformations that may be responsible for the change in a label or label element value, such as an assay result.

Figure 15:
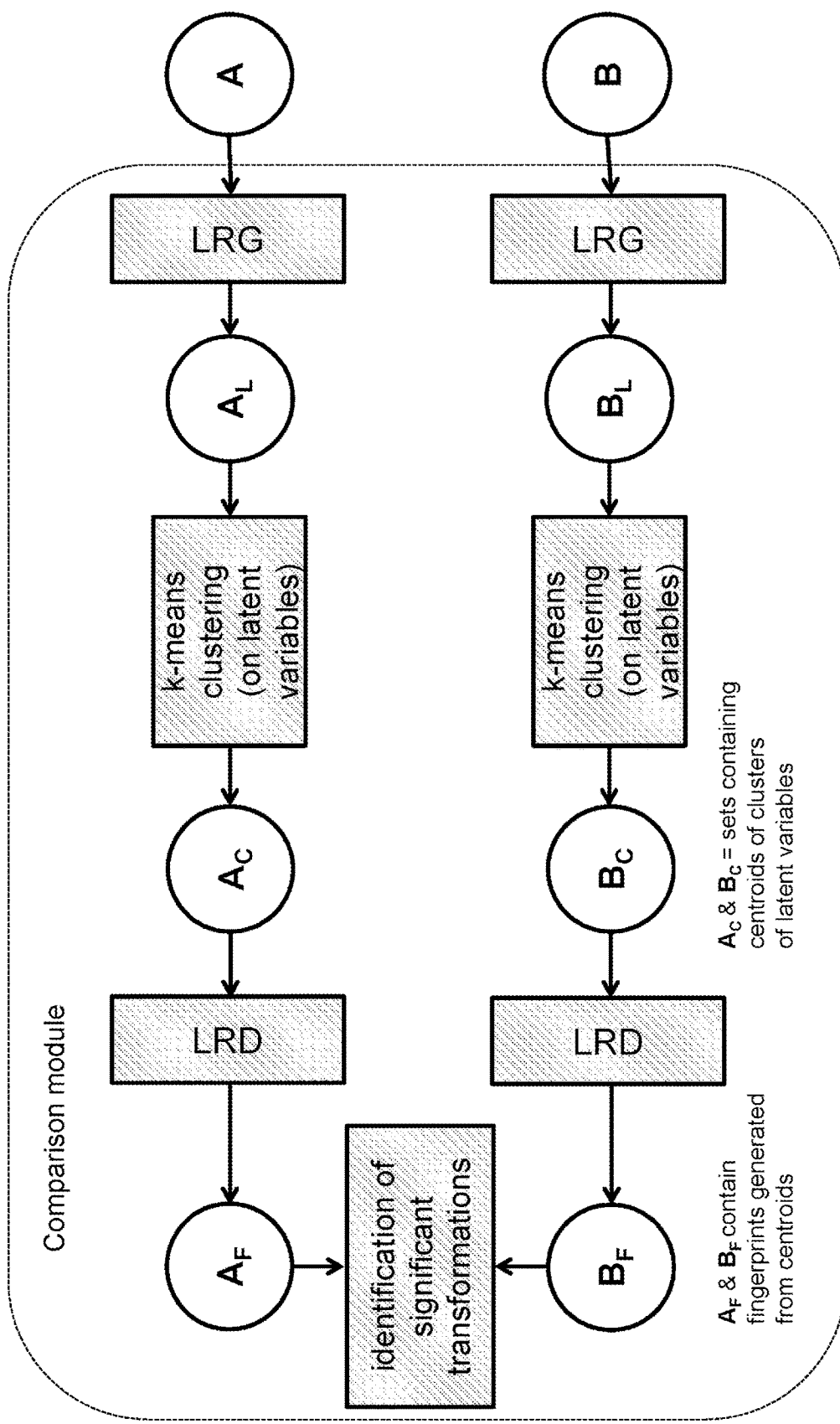
FIG. 15 depicts an exemplary illustration of a comparison module using k-means clustering.

In some cases, the systems and methods of the invention may be used to calculate a Gini coefficient using k-means clustering in the latent representation space. FIG. 15 depicts an exemplary illustration of a comparison module using k-means clustering. Accordingly, members of sets A and B may be encoded as latent representations, as may be the case in a k-medoids method. For example, a latent representation generator (LRG) may be used to encode the members of sets A and B as latent representations to form the latent representation sets $A_L$ and $B_L$, respectively. K-means clustering may be applied to the members of the latent representation sets. The centroids that result from k-means clustering may be extracted to form the latent representation centroid sets, $A_c$ and $B_c$. Without being bound by theory, the members of the centroid sets, Ae and Be may in many cases not be encoded latent representations corresponding to some members of the original sets A and B. However, the members of the centroid sets may be decoded to generate corresponding members in the compound representation space. For example, a latent representation decoder module (LRD) may be used to generate compound representations, e.g. fingerprints, corresponding to the centroids and these may be grouped in sets $A_F$ and $B_F$ respectively.

FIG. 9 depicts, in an exemplary embodiment, the training of an autoencoder on a large set of chemical compound representations. A latent representation decoder (LRD) may form the second part of the autoencoder, in a similar position as a decoder. That is during the training of the autoencoder, the decoder may learn to regenerate original compound representations from latent representations.

The generated representations in $A_F$ and $B_F$ may have relatively low-cardinality when compared to the original sets A and B. The members of the generated representations in $A_F$ and $B_F$ may be used to identify significant compound transformations.

In various embodiments, the systems and methods described herein deal with inputs of different make-up or length, for example labels having different label elements and/or a different number of label elements. For example, during training, different compounds in the training set may have labels of different lengths. A well-known drug may have many more assay results than a new compound. In addition, during the generation phase, a desired label y~ may be shorter than the labels $y^D$ used to train the model.

In various embodiments, a masking module, such as one employing a stochastic mask, may be used to bring various objects, for example, various labels, to uniformity with respect to length and/or make-up. In some cases, a probabilistic or variational autoencoder may become robust to missing values using a method similar to dropout.

In various embodiments, a stochastic mask can be used to generate masked versions of training labels $y^D$ prior to training. For example, a masking module may be configured to process a variety of labels prior to inputting them into a generative model. If two labels have a different number of label element values, a masking module may be used to add a value of zero to all of the label elements that are missing values. Further, the stochastic mask may be used to randomly zero out values of label elements during training By training a generative model in this way, the model may be able to process training labels and desired labels that initially may have varied in their number of label elements.

An exemplary embodiment of the masking module operates with assay results having binary outcomes. The assay results could be coded as label element values of −1 for inactivity and 1 for activity. The masking module may add a stochastic mask to each label element value in the training data set. With the mask, a label may be written as $y^D=(m_1 y_1, m_2 y_2, \ldots)$, where $y_i$ is the unmasked label element, $m_i$ is the mask for $y_i$, and wherein $m_i$ take values 0 or 1. For training, the values of $m_i$ may be set randomly, or they may be set following an empirical probability that the corresponding label element value is absent.

If $m_i y_i=0$, for the forward pass in backpropagation, no modification may be necessary because the 0 value may not contribute to the activation of the next layer. In order to avoid propagating the error to the node with the missing input value during the backward pass, an input node with a missing value may be flagged and disconnected during the backward pass. This training method may make the generative model able to process labels of different lengths during training and during a generation process.

Computer Systems

The present invention also relates to apparatus for performing the operations herein. This apparatus may be specially constructed for the required purposes, or it may comprise a general-purpose computer selectively activated or reconfigured by a computer program stored in the computer. Such a computer program may be stored in a computer readable storage medium, such as, but is not limited to, any type of disk including floppy disks, optical disks, CD-ROMs, and magnetic-optical disks, read-only memories (ROMs), random access memories (RAMs), EPROMs, EEPROMs, magnetic or optical cards, or any type of media suitable for storing electronic instructions, and each coupled to a computer system bus.

The descriptions presented herein are not inherently related to any particular computer or other apparatus. In addition to general-purpose systems, more specialized apparatus may be constructed to practice the various embodiments of the invention. In addition, the present invention is not described with reference to any particular programming language. It will be appreciated that a variety of programming languages may be used to implement the teachings of the invention as described herein. A machine-readable medium includes any mechanism for storing or transmitting information in a form readable by a machine (e.g., a computer). For example, a machine-readable medium includes read only memory ("ROM"); random access memory ("RAM"); magnetic disk storage media; optical storage media; flash memory devices; electrical, optical, acoustical or other form of propagated signals (e.g., carrier waves, infrared signals, digital signals, etc.); etc.

Figure 16:
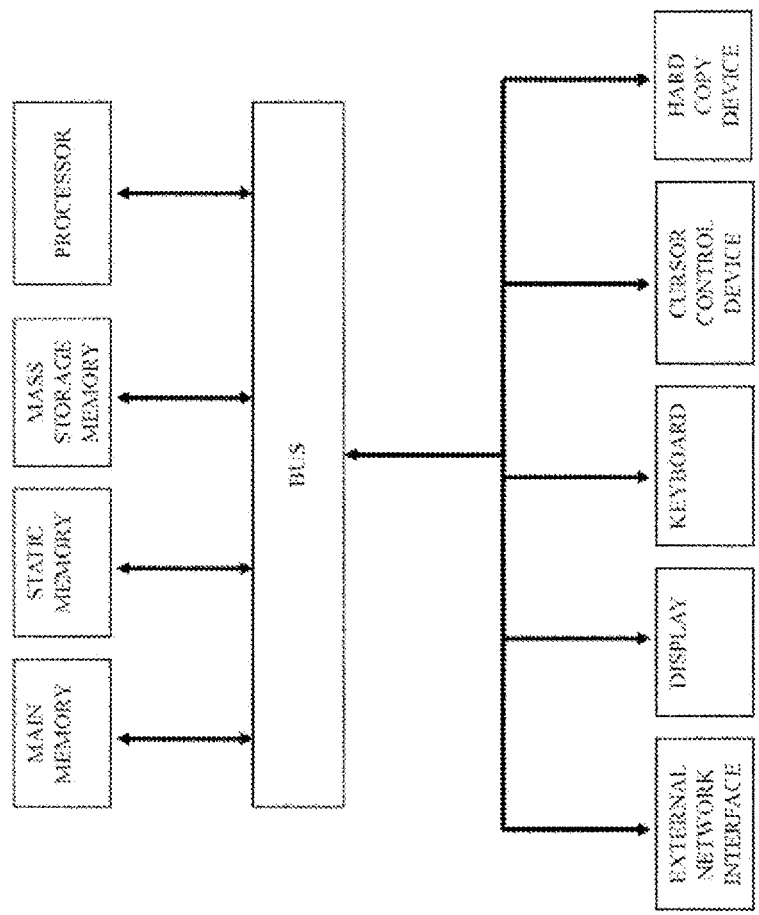
FIG. 16 is a block diagram of an exemplary computer system that may perform one or more of the operations described herein.

FIG. 16 is a block diagram of an exemplary computer system that may perform one or more of the operations described herein. Referring to FIG. 16, the computer system may comprise an exemplary client or server computer system. The computer system may comprise a communication mechanism or bus for communicating information, and a processor coupled with a bus for processing information. The processor may include a microprocessor, but is not limited to a microprocessor, such as, for example, Pentium, PowerPC, Alpha, etc. The system further comprises a random access memory (RAM), or other dynamic storage device (referred to as main memory) coupled to the bus for storing information and instructions to be executed by the processor. Main memory also may be used for storing temporary variables or other intermediate information during execution of instructions by the processor. In various embodiments, the methods and systems described herein utilize one or more graphical processing units (GPUs) as a processor. GPUs may be used in parallel. In various embodiments, the methods and systems of the invention utilize distributed computing architectures having a plurality of processors, such as a plurality of GPUs.

The computer system may also comprise a read only memory (ROM) and/or other static storage device coupled to the bus for storing static information and instructions for the processor, and a data storage device, such as a magnetic disk or optical disk and its corresponding disk drive. The data storage device is coupled to the bus for storing information and instructions. In some embodiments, the data storage devices may be located in a remote location, e.g. in a cloud server. The computer system may further be coupled to a display device, such as a cathode ray tube (CRT) or liquid crystal display (CD), coupled to the bus for displaying information to a computer user. An alphanumeric input device, including alphanumeric and other keys, may also be coupled to the bus for communicating information and command selections to the processor. An additional user input device is a cursor controller, such as a mouse, trackball, track pad, stylus, or cursor direction keys, coupled to the bus for communicating direction information and command selections to the processor, and for controlling cursor movement on the display. Another device that may be coupled to the bus is a hard copy device, which may be used for printing instructions, data, or other information on a medium such as paper, film, or similar types of media. Furthermore, a sound recording and playback device, such as a speaker and/or microphone may optionally be coupled to the bus for audio interfacing with the computer system. Another device that may be coupled to the bus is a wired/wireless communication capability for communication to a phone or handheld palm device.

Note that any or all of the components of the system and associated hardware may be used in the present invention. However, it can be appreciated that other configurations of the computer system may include some or all of the devices.

EXAMPLES

Example 1: Input Data for the Encoder During Training

In one example, data is provided to the encoder as pairs comprising a chemical compound representation ($x^D$), such as a fingerprint comprising a feature vector of molecular descriptors, and the label ($y^D$) associated with the represented compound. A pair input to the encoder may be described as IE=($x_i^D$, $y_i^D$), wherein $x_i^D$ is a real-valued vector with dimensionality $dim_{x_i^D}$ and wherein $y^D$ denotes label data for the corresponding $x_i^D$. The dimensionality of $x_i^D$, $dim_{x_i^D}$, may be fixed throughout a training data set. Elements of $y^D$ may be scalars or vectors optionally having arbitrary dimensions. Label element values in $y^D$ may be continuous or binary.

According to the descriptions in this example, for $x^D$ with dimension 10, and $y^D$ comprising a single label element value, an input data example may be as follows:

$x^D$=(1.2, −0.3, 1.5, 4.3, −2.9, 1.3, −1.5, 2.3, 10.2, 1.1), $y^D$=3, and
the input to the encoder is

IE=((1.2,−0.3,1.5,4.3,−2.9,1.3,−1.5,2.3,10.2,1.1),3).

Example 2: Output of Encoder During Training

An exemplary output structure for the encoder is described. For a given IE=($x_i^D$, $y_i^D$) input to the encoder, the encoder outputs a pair of a real-valued vector of means $\mu_{E,i}$ and a real-valued vector of standard deviations $\sigma_{E,i}$, represented as OE=($\mu_{E,i}$, $\sigma_{E,i}$)=(($\mu_{E,i,1}$, ..., $\mu_{E,i,d}$), ($\sigma_{E,i,1}$, ..., $\sigma_{E,i,d}$)). Dimensions of vectors $\mu_E$ and $v_E$ are the same in this example. However, the dimensions of vectors $\mu_E$ and $\sigma_E$ may be different than $dim_{x_i^D}$ or $dim_{x_i^D}$+$dim_{y_i^D}$. OE is provided by the encoder in a deterministic fashion. For a given IE and set of parameters of the encoder, a single OE pair is provided. For a dimensionality of 4, an exemplary output of encoder is illustrated by $\mu_E$=(1.2, −0.02, 10.5, 0.2) and $\sigma_E$=(0.4, 1.0, 0.3, 0.3).

Example 3: Creation of Latent Variable Z During Training Process

In this example, the means and standard deviations output by the encoder define a latent variable Z=(N($\mu_{E,i,1}$, $\sigma_{E,i,1}$), ..., N($\mu_{E,i,d}$, $\sigma_{E,i,d}$)), wherein $\mu_{E,i}$ and $\sigma_{E,i}$ are vectors output by the encoder and wherein N denotes a normal distribution. For example, if the output of the encoder comprises $\mu_E$=(1.2, −0.02, 10.5, 0.2) and $\sigma_E$=(0.4, 1.0, 0.3, 0.3), the sampling module may define a latent random variable as Z=(N(1.2, 0.4), N(−0.02, 1.0), N(10.5, 0.3), N(0.2, 0.3)).

Example 4: Generation of Latent Representations by Sampling Module During Training Process An exemplary sampling module draws a sample from a probability distribution or multiple samples from a set of probability distributions, such as those defined by latent variable Z and random variable X~. In this example, the sampling module may draw a sample from the latent variable Z to generate a latent representation z, which has the same dimension as latent variable Z. In this example, a single latent representation z is drawn from latent variable Z. For Z=(N(1.2, 0.4), N(−0.02, 1.0), N(10.5, 0.3), N(0.2, 0.3)) an exemplary latent representation vector z is z=(0.9, −0.1, 10.1, 0.1). If desired, the sampling module may draw multiple latent representations z from a single latent variable Z.

Example 5: The Input to the Decoder (ID) During Training

In this example, the decoder receives an input ID comprising an ordered pair (z, $y^D$), in which z is the latent representation sampled from the latent random variable Z, and $y^D$ is a label. In this example, the label $y^D$ is the same as the label associated with the input feature vector $x^D$. Therefore, the label $y^D$ is input twice in the training process: once to the encoder and once to the decoder. For example, ID may comprise the pair ((0.9, −0.1, 10.1, 0.1), 3).

The input layers of both the encoder and the decoder are configured such that they may receive both the fingerprint and its associated label. During comparative generation, this configuration facilitates the use of two different input labels: the original label $y^D$ is input to the encoder and the desired label y~ is input to the decoder.

Example 6: Output of Decoder During Training

In this example, the decoder generates as output a pair of a real-valued vector of means $\mu_{D,i}$ and a real-valued vector of standard deviations $\sigma_{D,i}$: OD=($\mu_{D,i}$, $\sigma_{D,i}$)=(($\mu_{D,i,1}$, ..., $\mu_{D,i,d}$), ($\sigma_{D,i,1}$, ..., $\sigma_{D,i,d}$)). The dimensions of the vectors $\mu_D$ and $\sigma_D$, in this example, are the same as the dimension of the feature vector $x^D$ that is input to the encoder. For example, if $dim_{x_i^D}$=10, the decoder may output $\mu_D$=(1.1, −0.2, 1.1, 3.9, −3.5, 0.1, −2.0, 1.9, 9.3, 1.0) and $\sigma_D$=(0.1, 0.3, 0.2, 0.5, 1.0, 0.5, 1.0, 0.2, 0.1, 1.0) for original input $x^D$=(1.2, −0.3, 1.5, 4.3, −2.9, 1.3, −1.5, 2.3, 10.2, 1.1).

From the output of the decoder, a latent variable X~ can be defined such that X~=(N($\mu_{D,i,1}$, $\sigma_{D,i,1}$), ..., N($\mu_{D,i,d}$, $\sigma_{D,i,d}$)), wherein $\mu_{D,i}$ and $\sigma_{D,i}$ are the vectors output by the decoder. For example, $\mu_D$=(1.1, −0.2, 1.1, 3.9, −3.5, 0.1, −2.0, 1.9, 9.3, 1.0) and $\sigma_D$=(0.1, 0.3, 0.2, 0.5, 1.0, 0.5, 1.0, 0.2, 0.1, 1.0), X~=(N(1.1, 0.1), N(−0.2, 0.3), . . . , N(1.0, 1.0)). The sampling module may then draw a sample x from X~, wherein x is a generated representation of a chemical compound.

Example 7: Sampling Latent Representation z from Standard Normal Distribution in Ab Initio Generation Procedure This example concerns the ab initio generation process. In this example, a latent representation z is drawn from a standard normal distribution N(0,1) by the sampling module. A single desired label y~ is used. For each chemical compound representation to be generated by the model, a separate latent representation z is drawn from N(0,1). For example, if the user wishes to generate two chemical compound representations, two separate latent representations, $z_1$ and $z_2$, are drawn from N(0,1). If the dimensionality of z is four, the sampling module may in one instance draw the samples $z_1$=(0.2, −0.1, 0.5, 0.1) and $z_2$=(0.3, 0.1, 0, −0.3).

Example 8: Input to Decoder in Ab Initio Generation Process

In this example, the latent representation z, previously sampled from N by the sampling module, as well as the desired label, y~, are input to the decoder. The label y~ may be specified by the user according to the desired properties and activities of the compound represented by the generated fingerprint. The desired label y~ must contain desired values for a subset of the label elements that were used to train the model, i.e., the label elements contained in label $y^D$. If y~ has fewer label elements than $y^D$, the masking module may give the missing label elements of y~ a value of 0, prior to y~ being input to the decoder. The desired label y~ may contain one or more values of label elements that differ from the values of the corresponding label elements in $y^D$. It is possible to draw multiple samples z from N in order to generate multiple x~ with a single desired label y~. It is also possible to generate more than one chemical compound representation from a single latent representation z by inputting to the decoder a number of pairs consisting of z and different desired labels y~ and generating more than one random variable X~.

Example 9: Output of Decoder in Ab Initio Generation Procedure

In this example, the decoder outputs a pair of a real-valued vector of means $\mu_D\tilde{}$ and a real-valued vector of standard deviations $\sigma_D\tilde{}$, ($\mu_D\tilde{}$, $\sigma_D\tilde{}$). In this example, the dimension of vectors $\mu_D\tilde{}$ and $\sigma_D\tilde{}$ is the same as the dimension of the feature vectors $x^D$, which are the fingerprints used in the training of the model. For example, if the dimension of $x^D$ is 10, the decoder may in one instance output $\mu_D\tilde{}$=(1.1, −0.2, 1.1, 3.9, −3.5, 0.1, −2.0, 1.9, 9.3, 1.0) and $\sigma_D\tilde{}$=(0.1, 0.3, 0.2, 0.5, 1.0, 0.5, 1.0, 0.2, 0.1, 1.0).

Example 10: Construction of Random Variable X~ in Ab Initio Generation Procedure From the output of the decoder, a random variable X~ can be defined such that X~=(N($\mu_{D,i,1}$, $\sigma_{D,i,1}$), . . . , N($\mu_{D,i,d}$, $\sigma_{D,i,d}$)), wherein $\mu_{D,i}$ and $\sigma_{D,i}$ are the vectors output by the decoder. For example, if $\mu_D$=(1.1, −0.2, 1.1, 3.9, −3.5, 0.1, −2.0, 1.9, 9.3, 1.0) and $\sigma_D$=(0.1, 0.3, 0.2, 0.5, 1.0, 0.5, 1.0, 0.2, 0.1, 1.0), X~=(N(1.1, 0.1), N(−0.2, 0.3), . . . , N(1.0, 1.0)).

Example 11: Sampling from Random Variable X~ to Generate Representations x~ in Ab Initio Generation Process To generate a chemical compound representation x~, the sampling module draws a sample from random variable X~. Defining X~ such that its dimension is the same as that of the fingerprint feature vectors used to train the model may allow for the dimension of representation x~ to be the same as that of the fingerprint feature vectors. If desired, a plurality of chemical compound representations may be sampled from random variable X~. For example, if random variable X~=(N(1.1, 0.1), N(−0.2, 0.3), . . . , N(1.0, 1.0)), four samples may be drawn from X~, yielding in one instance, the four representations $x_1\tilde{}$=(1.0, −0.1, . . . , 3.0), $x_2\tilde{}$=(1.2, −0.5, . . . , 1.8), $x_3\tilde{}$=(1.0, −0.1, . . . , 0.5), and $x_4\tilde{}$=(0.9, 0.3, . . . , 1.1).

Example 12: Input and Output of Encoder in Comparative Generation Procedure

In this example, inputs to the encoder and outputs from the encoder are of the same types as were used in Examples 1 and 2 during training of the encoder and decoder. For example:
  $x_D$=(1.2, −0.3, 1.5, 4.3, −2.9, 1.3, −1.5, 2.3, 10.2, 1.1),
  $y_D$=3,
  $\mu_E$=(1.2, −0.02, 10.5, 0.2), and
  $\sigma_E$=(0.4, 1.0, 0.3, 0.3).

However, while the inputs to the encoder and outputs from the encoder are used in Examples 1 and 2 for training the generative model, in this example they are used in the process of generating novel chemical compound representations.

Example 13: Construction of Latent Variable Z and Sampling of Latent Representation z in Comparative Generation Procedure In this example, the same procedures are used to define the latent variable Z and to sample from Z in order to create latent representation z, as are used in Examples 3 and 4 above.
For Example:
  $\mu_E$=(1.2, −0.02, 10.5, 0.2),
  $\sigma_E$=(0.4, 1.0, 0.3, 0.3),
  Z=(N(1.2, 0.4), N(−0.02, 1.0), N(10.5, 0.3), N(0.2, 0.3)), and
  z=(0.9, −0.1, 10.1, 0.1).

However, while latent variable Z and latent representation z were used in Examples 3 and 4 to train the generative model, in this example they are used in the process of generating chemical compound representations. If desired, a plurality of latent representations z may be drawn from latent variable Z.

Example 14: Input and Output of Decoder in Comparative Generation Procedure

In this example, the same procedures as were used in Examples 8 and 9 are used to construct both the input to, and the output of, the decoder. For example:
  ID=(z, y~),
  OD=($\mu_D\tilde{}$, $\sigma_D\tilde{}$), $\mu_D\tilde{} = (1.1, -0.2, 1.1, 3.9, -3.5, 0.1, -2.0, 1.9, 9.3, 1.0)$, and
$\sigma_D\tilde{} = (0.1, 0.3, 0.2, 0.5, 1.0, 0.5, 1.0, 0.2, 0.1, 1.0)$.

As in Examples 9, 10, and 11, the output of the decoder is used to generate chemical compound representations. However, while in Example 8 latent representation z is drawn from a standard normal distribution, in this example it is drawn from latent variable Z, which is a latent variable over the seed compound $x^D$ and its associated label $y^D$. The sampling module draws a sample from latent variable Z to generate latent representation z. One or more latent representations z may be drawn from latent variable Z, and paired with one or more desired labels y~ in various combinations in order to generate a plurality of outputs from the decoder.

Example 15: Construction of Random Variable X~ and Sampling of Chemical Compound Representation x~ in Comparative Generation Procedure In this example, the same procedures as were used in Examples 10 and 11 are used to define random variable X~ and to generate chemical compound representation x~ by sampling from X~. For example:

$X\tilde{} = (N(1.1, 0.1), N(-0.2, 0.3), \ldots, N(1.0, 1.0))$,
$x_1\tilde{} = (1.0, -0.1, \ldots, 3.0)$,
$x_2\tilde{} = (1.2, -0.5, \ldots, 1.8)$,
$x_3\tilde{} = (1.0, -0.1, \ldots, 0.5)$, and
$x_4\tilde{} = (0.9, 0.3, \ldots, 1.1)$.

In the ab initio generation process described in Example 11, random variable X~ is created from only an essentially random latent representation and the desired label y~. Therefore, the compound identified by generated chemical compound representation x~ is expected only to have activities and properties that conform to the requirements of desired label y~. However, in the present Example 15, random variable X~, and therefore chemical compound representation x~, are created from both a specified seed compound $x^D$ and its associated label $y^D$. Therefore, in the comparative generation procedure of the present example, generated chemical compound representation x~ can be expected both to retain some salient aspects of the seed compound $x^D$ and to have activities and properties that conform to the requirements of desired label y~.

Example 16: Evaluation of Predicted Results of Generated Compounds Followed by Ranking In this example, the predicted assay results of generated fingerprints are compared to the desired assay results. Fingerprints having predicted results that match the desired assay results are then ranked by a druglikeness score.

After generation of fingerprint x~, for example through ab initio or comparative generation, x~ is input to the trained predictor module. (The predictor module may, for example, have been trained during a semi-supervised learning process for unlabeled data.) The predictor module outputs y^, the predicted set of assay results for the generated fingerprint x~.

The predicted assay results y^ and the desired assay results y~ are input to the comparison module (FIG. 7). If the predicted results are the same as the desired results, x~ is added to the set of unranked candidates, U; otherwise, x~ is rejected. The unranked set is then ranked by the ranking module, for example as described in EXAMPLE 18.

Example 17: Evaluation of Fingerprints Generated Through Comparative Generation In this example, fingerprints generated using a comparative generation process are evaluated for similarity to the seed compound and for having a label similar to a desired label. In a comparative generation procedure exemplified above, a seed compound is used to generate a novel fingerprint that is similar to the seed. Once the fingerprint is generated, an additional evaluation step is used to determine whether the generated fingerprint is sufficiently similar to the seed. A comparison module is used to compare corresponding parameters of the two fingerprints. If a threshold of identical parameters or a threshold similarity is reached, the two fingerprints are marked as sufficiently similar.

After the generation of fingerprint x~, both x~ and $x^D$, the seed compound, are input to the comparison module. If x~ is sufficiently similar to $x^D$, it is retained; otherwise it is rejected. If retained, x~ is input to a predictor module, and a predicted label y^ is provided by the predictor module. A comparison module is used to compare the predicted label y^ to the desired label y~. If the predicted label y^ is sufficiently similar to or the same as the desired label y~, x~ is added to the unranked candidate set, U. The unranked set of fingerprints is then ranked by the ranking module to output a ranked set, R.

Example 18: Training of a Ranking Module and a Ranking Module Application

In this example a ranking module is trained to rank generated representations x~. The generated representations may have been filtered by other modules, such as comparison modules, prior to entering the ranking module. The ranking module, in this example, has two functions: (1) to assign a druglikeness score to each fingerprint, and (2) to rank a set of fingerprints according to their druglikeness scores.

The ranking module is configured to evaluate fingerprints based on their latent representations.

First, an autoencoder is trained on a large set of compound fingerprints. After training, the first half of the autoencoder, the LRG, is used to generate latent representations of chemical compounds (FIG. 9). The latent representation is input to the classifier and the classifier is trained with supervised learning. The training data set comprises the approximately 2,500 FDA-approved drugs, all of which have the class label Drug, and a large set of other non-drug compounds, all of which have the label Not Drug. The classifier outputs a continuous score that represents the compound's druglikeness. To apply the ranking module, members of the unranked set of generated compound fingerprints are input to the latent representation generator (LRG) and the generated latent representations are then input to the classifier. Each compound receives a druglikeness score from the classifier. The compounds are then ordered from highest score to lowest score. The final output is a ranked set of candidate compound fingerprints.

Example 19: Sequential Application of Ab Initio and Comparative Generation to Explore a Novel Compound Space For a certain set of assay results, it may be desirable to generate a novel compound that satisfies those results, and then explore similar compounds in the space surrounding the initial compound. For this application, ab initio and comparative generation may be used in sequence.

Based on a desired assay result y~, fingerprint x~ is generated using ab initio generation (FIG. 11). In order to identify previously unknown compounds, the comparison module compares x~ to a database of known compounds. If x~ already exists in the database, it is rejected. If x~ is a previously unknown compound, it is input to the predictor to generate predicted assay results y^.

Fingerprint x~ and its predicted assay results y^ are then used as the seeds for comparative generation. A new fingerprint x+ is generated, along with its predicted assay results y+. The comparison module then determines whether y+ is the same as the desired assay results y~. If it is, x+ is retained and added to the set of unranked candidates. Any desired number of fingerprints x+ may be generated from the initial seed of x~ and y^ by repeated application of comparative generation.

After the desired number of candidates has been generated and collected as a set of unranked candidate fingerprints U, the unranked set is input to the ranking module, which outputs the ranked set R.

Example 20: QSAR Analysis—Part I: Identification of Compound Properties that May Affect Results on a Specific Assay This method is used to identify compound properties that may be responsible for a particular assay result. This method provides a way to identify candidate transformations, i.e. specific structural properties that change a compound's performance on a particular assay. These may then be used as a starting point for Matched Molecular Pair Analysis (MMPA).

In this example, two ab initio generation processes are run in parallel. In one, the desired assay result, y~, is used as the positive seed. In the other, the opposite assay result, y*, is used as the negative seed. If y~ is a single binary assay result, the negative seed y* is the opposite result for that assay. To reduce variability in the resulting generated fingerprints, a vector of assay results may be used as the positive seed, y~. In this case, y* differs from y~ by only a single result on an assay of interest.

Two sets of compound fingerprints, A and B, are generated: A contains compounds generated from the positive seed, y~, while B contains compounds generated from the negative seed, y*. After generating the desired number of members for each set, the two sets are input to a comparison module. The comparison module identifies the fingerprint parameters that are most likely responsible for the difference in the assay result of interest. Exemplary comparison modules are described in further detail in subsequent examples and elsewhere herein.

Example 21: QSAR Analysis—Part II: Exploration of Transformations Related to a Desired Result for a Specific Compound In this example, a method is described for exploring transformations in a specific compound that may be responsible for a specific assay result. In this method, two comparative generation processes are run in parallel repeatedly to generate two sets of fingerprints (FIG. 13). These processes use the same seed compound, but each uses a different set of target assay results, for example, a positive target y~ and a negative target y* for which y~ and y* differ by a single assay result. A comparison module is used to identify specific structural differences between fingerprints generated with the positive target and those generated with the negative target.

The generated fingerprints are evaluated first by their similarity to the seed compound. If the comparison module finds them to be sufficiently similar to the seed compound, a predictor is used to provide predicted assay results for each generated fingerprint. The predicted assay results are checked for similarity or identity with the corresponding target assay result y~ and y*, respectively.

The comparative generation processes are run as many times as needed in order to generate two sets of candidate fingerprints, A and B, with the desired cardinality, where A contains generated fingerprints created with the positive target y~, and B contains generated fingerprints created with the negative target, y*. The members of A are compared to the members of B using a comparison module. The comparison module is configured to identify consistent and differing structural transformations within the two sets. These structural transformations can then be used as the starting point for further analysis through MMPA.

Example 22: Comparison Module

This example describes a comparison module having two functions (1) determining whether two objects, e.g. two vectors of assay results or two fingerprints, are similar or identical, and (2) identifying fingerprint parameters that are most probable to be responsible for a change in a specified assay result by comparing two sets of fingerprints.

A. Comparison of Two Objects for Similarity

In a simple pairwise comparison for similarity, the corresponding elements of the two objects, e.g. either two vectors of assay results or two fingerprints are compared. A user-specified threshold is set to determine whether the two objects pass or fail the comparison.

A second method for comparing two fingerprints uses the Latent Representation Generator (LRG) to encode the fingerprints as latent representations. The corresponding distributions of the latent representations are then compared and a determination of similarity is made.

B. Comparison of Sets of Objects for Identification of Significant Compound Transformations A number of methods may be used to identify significant compound transformations when comparing two sets of fingerprints. One simple method is to use a linear model to identify significant parameters. For example, to address the possibility that interactions between parameters were responsible for the change in an assay result, interaction terms could be added to the model.

A second method involves the use of the Gini coefficient. The Gini coefficient is calculated for each parameter by calculating the mean of the differences between every possible pair of fingerprints, divided by the mean size. The parameters with the largest Gini coefficients are selected as the parameters most likely to be related to the change in assay result.

In an extension of this method, a classification tree is used. The parameter with the largest Gini coefficient is selected to be the root of a classification tree. The remainder of the classification tree is learned by top-down induction. The desired number of significant parameters is then identified by the observing the behavior of the tree at a suitable level.

When the two sets of fingerprints have low cardinality, the Gini coefficient may be directly calculated. In some cases, a clustering method is applied to reduce the number of required pairwise comparisons between A and B. The Gini coefficients of the parameters are then calculated by pairwise comparisons between the centroids of A and B.

Example 23: Calculation of Gini Coefficient Using k-Medoids Clustering

In this example, the comparison module is configured to utilize clusters of the latent representations of the sets A and B. First, a latent representation generator (LRG) is used to encode the members of sets A and B as latent representations to form the sets $A_L$ and $B_L$, respectively (FIG. 14). K-medoids clustering is then applied to the members of the sets $A_L$ and $B_L$. Following clustering, the centroids of the clustered sets are extracted to form the latent representation centroid sets $A_c$ and $B_c$. The fingerprints corresponding to the members of $A_c$ and $B_c$ are looked up to form two sets of fingerprints $A_F$ and $B_F$. The members of sets $A_F$ and $B_F$ are then used to identify compound transformations that may be responsible for the change in an assay result or another label element value.

Example 24: Calculation of Gini Coefficient Using k-Means Clustering

In this example, k-means clustering is used instead of the k-medoids clustering in the method described in EXAMPLE 23. As in the k-medoids method, the members of sets A and B are encoded as latent representations. K-means clustering is applied to the sets of latent representations. The centroids that result from k-means clustering are decoded as fingerprints by using the latent representation decoder module (LRD) and saved in respective sets $A_F$ and $B_F$. Sets $A_F$ and $Z_F$ are used to identify significant compound transformations that are associated with changes in a label or label element value.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A computer system comprising:
one or more memories; and
one or more processors configured to:
cause a generative model to generate structural information regarding a chemical compound by inputting a latent representation into the generative model,
wherein the generative model has been trained such that differences between structural information regarding other chemical compounds and reconstructions of the structural information regarding the other chemical compounds generated by the generative model are reduced, the reconstructions being generated by inputting latent representations into the generative model, the latent representations being generated based on the structural information regarding the other chemical compounds,
wherein the structural information regarding the chemical compound expresses, and uniquely identifies, a chemical structure of atoms and bonds of the chemical compound, and
wherein the generative model is a deep-neural-network-based decoder that decodes the latent representation into the structural information regarding the chemical compound that expresses, and uniquely identifies, the chemical structure of the atoms and bonds of the chemical compound.

2. The computer system as claimed in claim 1, wherein the latent representation input into the generative model includes one or more random values.

3. The computer system as claimed in claim 1, wherein the one or more processors are further configured to generate the latent representation input into the generative model based on structural information regarding another chemical compound.

4. The computer system as claimed in claim 1, wherein the one or more processors are further configured to generate the latent representation input into the generative model by sampling from a latent variable.

5. The computer system as claimed in claim 4, wherein the latent variable is modeled by one of a Normal distribution, a Laplace distribution, an Elliptical distribution, a Student's t distribution, a Logistic distribution, a Uniform distribution, a Triangular distribution, an Exponential distribution, an Invertible cumulative distribution, a Cauchy distribution, a Rayleigh distribution, a Pareto distribution, a Weibull distribution, a Reciprocal distribution, a Gompertz distribution, a Gumbel distribution, an Erlang distribution, a Logarithmic Normal distribution, a Gamma distribution, a Dirichlet distribution, a Beta distribution, a Chi-Squared distribution, or an F distribution.

6. The computer system as claimed in claim 4, wherein the one or more processors are further configured to generate the latent variable based on another chemical compound.

7. The computer system as claimed in claim 1, wherein the one or more processors are configured to cause the generative model to generate the structural information regarding the chemical compound by inputting the latent representation and label information into the generative model.

8. The computer system as claimed in claim 7, wherein the label information includes at least one of a property or an activity of a desired chemical compound to be generated.

9. The computer system as claimed in claim 7, wherein the label information includes at least one of a bioassay result, toxicity, cross-reactivity, pharmacokinetics, pharmacodynamics, bioavailability, or solubility.

10. The computer system as claimed in claim 7, wherein the one or more processors are further configured to generate the label information based on another chemical compound.

11. The computer system as claimed in claim 10, wherein the one or more processors are further configured to generate the label information by using a predictor.

12. The computer system as claimed in claim 7, wherein the one or more processors are further configured to generate the latent representation input into the generative model based on another chemical compound, and the label information input into the generative model includes information different from label information of the another chemical compound.

13. The computer system as claimed in claim 1, wherein the structural information regarding the chemical compound is a feature vector including information regarding the chemical structure of the atoms and bonds of the chemical compound.

14. A method of generating structural information regarding a chemical compound, comprising:
causing, by at least one processor, a generative model to generate the structural information regarding the chemical compound by inputting a latent representation into the generative model,
wherein the generative model has been trained such that differences between structural information regarding other chemical compounds and reconstructions of the structural information regarding the other chemical compounds generated by the generative model are reduced, the reconstructions being generated by inputting latent representations into the generative model, the latent representations being generated based on the structural information regarding the other chemical compounds, wherein the structural information regarding the chemical compound expresses, and uniquely identifies, a chemical structure of atoms and bonds of the chemical compound, and wherein the generative model is a deep-neural-network-based decoder that decodes the latent representation into the structural information regarding the chemical compound that expresses, and uniquely identifies, the chemical structure of the atoms and bonds of the chemical compound.

15. The method as claimed in claim 14, wherein the causing, by the at least one processor, the generative model to generate the structural information regarding the chemical compound includes causing, by the at least one processor, the generative model to generate the structural information regarding the chemical compound by inputting the latent representation and label information into the generative model.

16. The method as claimed in claim 14, wherein the latent representation input into the generative model includes one or more random values.

17. The method as claimed in claim 14, further comprising generating, by the at least one processor, the latent representation input into the generative model based on structural information regarding another chemical compound.

18. The method as claimed in claim 14, further comprising generating, by the at least one processor, the latent representation input into the generative model by sampling from a latent variable.

19. The method as claimed in claim 18, wherein the latent variable is modeled by one of a Normal distribution, a Laplace distribution, an Elliptical distribution, a Student's t distribution, a Logistic distribution, a Uniform distribution, a Triangular distribution, an Exponential distribution, an Invertible cumulative distribution, a Cauchy distribution, a Rayleigh distribution, a Pareto distribution, a Weibull distribution, a Reciprocal distribution, a Gompertz distribution, a Gumbel distribution, an Erlang distribution, a Logarithmic Normal distribution, a Gamma distribution, a Dirichlet distribution, a Beta distribution, a Chi-Squared distribution, or an F distribution.

20. The method as claimed in claim 18, further comprising generating, by the at least one processor, the latent variable based on another chemical compound.

21. The method as claimed in claim 15, wherein the label information includes at least one of a property or an activity of a desired chemical compound to be generated.

22. The method as claimed in claim 15, wherein the label information includes at least one of a bioassay result, toxicity, cross-reactivity, pharmacokinetics, pharmacodynamics, bioavailability, or solubility.

23. The method as claimed in claim 15, further comprising generating, by the at least one processor, the label information based on another chemical compound.

24. The method as claimed in claim 23, further comprising generating, by the at least one processor, the label information by using a predictor.

25. The method as claimed in claim 15, further comprising generating, by the at least one processor, the latent representation input into the generative model based on another chemical compound, and the label information input into the generative model includes information different from label information of the another chemical compound.

26. The method as claimed in claim 14, wherein the structural information regarding the chemical compound is a feature vector including information regarding the chemical structure of the atoms and bonds of the chemical compound.

27. The method as claimed in claim 14, further comprising:

generating, by the at least one processor, the latent representations based on the structural information regarding the other chemical compounds, generating, by the at least one processor, the reconstructions by inputting the latent representations into the generative model, and training, by the at least one processor, the generative model such that the differences between the structural information regarding the other chemical compounds and the reconstructions are reduced.

28. The computer system as claimed in claim 1, wherein the one or more processors are further configured to:

generate the latent representations based on the structural information regarding the other chemical compounds, generate the reconstructions by inputting the latent representations into the generative model, and train the generative model such that the differences between the structural information regarding the other chemical compounds and the reconstructions are reduced.

29. A non-transitory computer-readable recording medium having a program embodied therein for causing one or more computers to cause a generative model to generate structural information regarding a chemical compound by inputting a latent representation into the generative model, wherein the generative model has been trained such that differences between structural information regarding other chemical compounds and reconstructions of the structural information regarding the other chemical compounds generated by the generative model are reduced, the reconstructions being generated by inputting latent representations into the generative model, the latent representations being generated based on the structural information regarding the other chemical compounds, wherein the structural information regarding the chemical compound expresses, and uniquely identifies, a chemical structure of atoms and bonds of the chemical compound, and wherein the generative model is a deep-neural-network-based decoder that decodes the latent representation into the structural information regarding the chemical compound that expresses, and uniquely identifies, the chemical structure of the atoms and bonds of the chemical compound.

* * * * *